US009323890B2

(12) United States Patent
Hayashi

(10) Patent No.: US 9,323,890 B2
(45) Date of Patent: Apr. 26, 2016

(54) OPTIMAL SOLUTION SEARCH METHOD AND OPTIMAL SOLUTION SEARCH DEVICE

(71) Applicant: Naoki Hayashi, Kanagawa (JP)

(72) Inventor: Naoki Hayashi, Kanagawa (JP)

( * ) Notice: Subject to any disclaimer, the term of this patent is extended or adjusted under 35 U.S.C. 154(b) by 0 days.

(21) Appl. No.: 14/349,325

(22) PCT Filed: Oct. 5, 2012

(86) PCT No.: PCT/JP2012/075974
§ 371 (c)(1),
(2) Date: Apr. 2, 2014

(87) PCT Pub. No.: WO2013/051701
PCT Pub. Date: Apr. 11, 2013

(65) Prior Publication Data

US 2014/0258279 A1 Sep. 11, 2014

(30) Foreign Application Priority Data

Oct. 7, 2011 (JP) ................................ 2011-223215

(51) Int. Cl.
*G06F 19/28* (2011.01)
*G06N 3/12* (2006.01)

(52) U.S. Cl.
CPC ................ *G06F 19/28* (2013.01); *G06N 3/126* (2013.01)

(58) Field of Classification Search
None
See application file for complete search history.

(56) References Cited

U.S. PATENT DOCUMENTS

2007/0094161 A1* 4/2007 Calabro et al. .................. 706/13

FOREIGN PATENT DOCUMENTS

| | | | |
|---|---|---|---|
| JP | 07-205953 | A | 11/1995 |
| JP | 11-168505 | A | 6/1999 |
| JP | 2000-172852 | A | 6/2000 |
| JP | 2001-249970 | A | 9/2001 |
| JP | 2009-010611 | A | 1/2009 |

OTHER PUBLICATIONS

Yu, Hongmei, et al, "A combined genetic algorithm/simulated annealing algorithm for large scale system energy integration" Computers and Chemical Engineering 24 (2000) p. 2023-2035.*

Li, Xiaodong, "A Real-Coded Predator-Prey Genetic Algorithm for Multiobjective Optimization" C.M. Fonseca et al. (Eds.): EMO 2003, LNCS 2632, pp. 207-221, 2003.*

(Continued)

*Primary Examiner* — Kakali Chaki
*Assistant Examiner* — Isidore Sobkowski
(74) *Attorney, Agent, or Firm* — Knobbe Martens Olson and Bear, LLP

(57) ABSTRACT

A search device and method of a pertinent solution using a genetic algorithm that performs genetic operation(s) on a plurality of individuals each having an element of a candidate solution to a problem in the form of a gene sequence. Genetic information about target individuals includes whether all individuals are, regardless of their fitness values, in a state among a living state that is a target of genetic operation and a target of calculating a fitness value, and a dead state that is not the target of genetic operation nor the target of the calculation of the fitness value. Each target individual has a predetermined value of a lifespan. A breeding area that allows predation of leading an individual belonging to a lower layer to a dead state due to predation by an individual belonging to a higher layer in the breeding area is an aspect of generating new target individuals.

17 Claims, 12 Drawing Sheets

100

10 CPU
11 INPUT DEVICE
12 DISPLAY DEVICE
13 STORAGE DEVICE
50

13
E2
IN CROSSOVER MUTATION LIFESPAN TR
IN MUTATION PREDATION 1 LIFESPAN MR
IN PREDATION 2 CROSSOVER BR

(56) References Cited

OTHER PUBLICATIONS

Beasley, David et al "An Overview of Genetic Algorithms: Part 1, Fundamentals," University of Cardiff, University Computing, 1993.*
Schultz, A, et al, "Improving tactical plans with genetic algorithms" Tools for Artificial Intelligence, 1990, Proceeding of the 2nd International Conference, 1990, pp. 328-334.*
Arabas, Jaroslaw et al., GAVaPS—a Genetic Algorithm With Varying Population Size, Evolutionary Computation, IEEE World Congress on Computation Intelligence, Proceedings of the First IEEE Conference on, Jun. 1994, pp. 73-78, vol. 1.
Choi, Daiseub et al., The Application of a Genetic Algorithm with a Chromosome Limited Life for the Distribution System Loss Minimization Re-configuration Problem, The Transactions of the Institute of Electrical Engineers of Japan. B, A Publication of Power and Energy Society, Jun. 20, 1995, pp. 741-748, vol. 115-B, No. 7.
Omori, Kiyohiro et al., Parallelization of genetic Algorithm with Sexual Selection, The Transactions of the Institute of Electrical Engineers of Japan. C, A Publication of Electronics, Information and System Society, Nov. 1, 2003, pp. 2020-2027, vol. 123, No. 11.
PCT, International Search Report for International Application No. PCT/JP2012/075974, dated Dec. 18, 2012.

* cited by examiner 100
10
CPU
11
INPUT DEVICE
12
DISPLAY DEVICE
13
STORAGE DEVICE
50

13
CROSSOVER
IN
MUTATION
LIFESPAN
TR
IN
PREDATION 1
MUTATION
LIFESPAN
E2
MR
IN
PREDATION 2
CROSSOVER
BR

IN

GI
21a
22a
23a
24a
2xa
ID

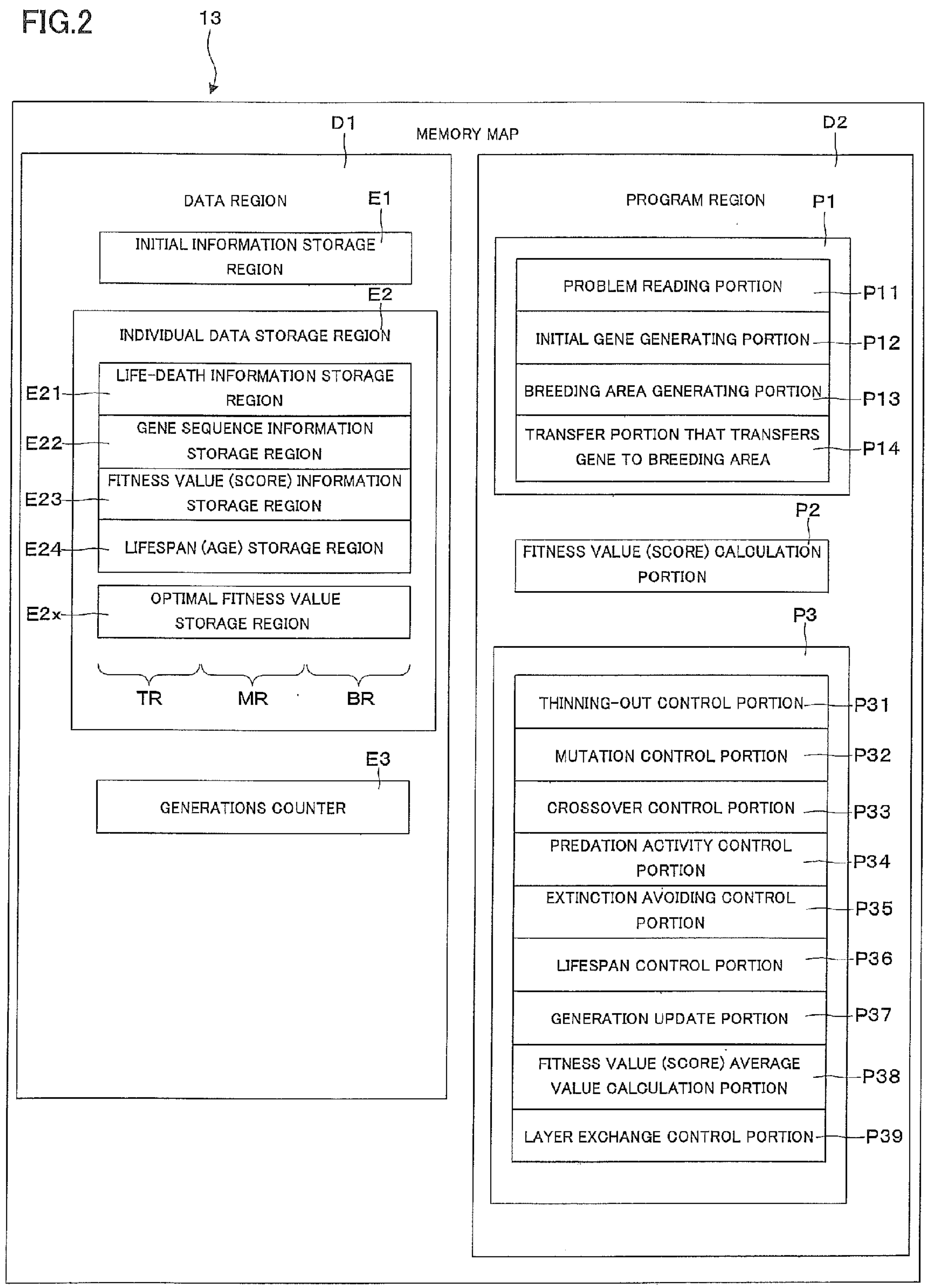
FIG.2
13
MEMORY MAP
D1
DATA REGION
E1
INITIAL INFORMATION STORAGE REGION
E2
INDIVIDUAL DATA STORAGE REGION
E21
LIFE-DEATH INFORMATION STORAGE REGION
E22
GENE SEQUENCE INFORMATION STORAGE REGION
E23
FITNESS VALUE (SCORE) INFORMATION STORAGE REGION
E24
LIFESPAN (AGE) STORAGE REGION
E2x
OPTIMAL FITNESS VALUE STORAGE REGION
TR
MR
BR
E3
GENERATIONS COUNTER
D2
PROGRAM REGION
P1
PROBLEM READING PORTION
P11
INITIAL GENE GENERATING PORTION
P12
BREEDING AREA GENERATING PORTION
P13
TRANSFER PORTION THAT TRANSFERS GENE TO BREEDING AREA
P14
P2
FITNESS VALUE (SCORE) CALCULATION PORTION
P3
THINNING-OUT CONTROL PORTION
P31
MUTATION CONTROL PORTION
P32
CROSSOVER CONTROL PORTION
P33
PREDATION ACTIVITY CONTROL PORTION
P34
EXTINCTION AVOIDING CONTROL PORTION
P35
LIFESPAN CONTROL PORTION
P36
GENERATION UPDATE PORTION
P37
FITNESS VALUE (SCORE) AVERAGE VALUE CALCULATION PORTION
P38
LAYER EXCHANGE CONTROL PORTION
P39

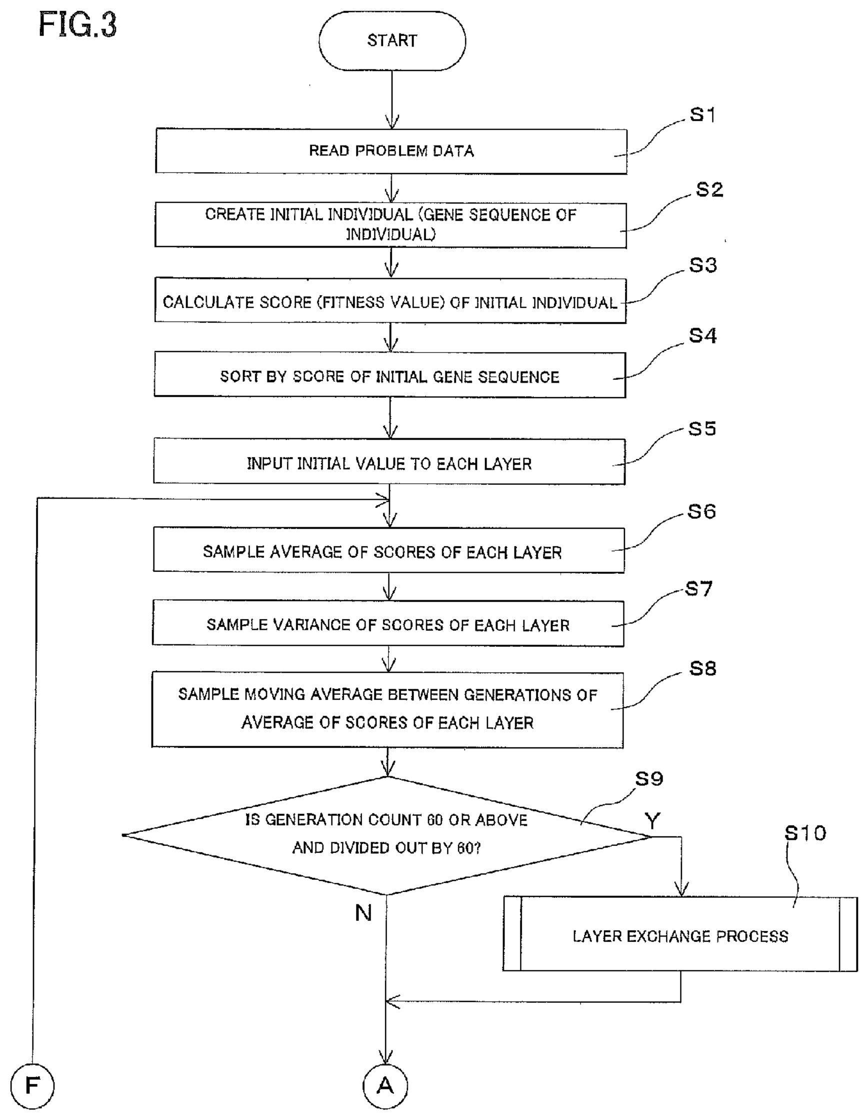
FIG.3
START
S1
READ PROBLEM DATA
S2
CREATE INITIAL INDIVIDUAL (GENE SEQUENCE OF INDIVIDUAL)
S3
CALCULATE SCORE (FITNESS VALUE) OF INITIAL INDIVIDUAL
S4
SORT BY SCORE OF INITIAL GENE SEQUENCE
S5
INPUT INITIAL VALUE TO EACH LAYER
S6
SAMPLE AVERAGE OF SCORES OF EACH LAYER
S7
SAMPLE VARIANCE OF SCORES OF EACH LAYER
S8
SAMPLE MOVING AVERAGE BETWEEN GENERATIONS OF AVERAGE OF SCORES OF EACH LAYER
S9
IS GENERATION COUNT 60 OR ABOVE AND DIVIDED OUT BY 60?
Y
N
S10
LAYER EXCHANGE PROCESS
F
A

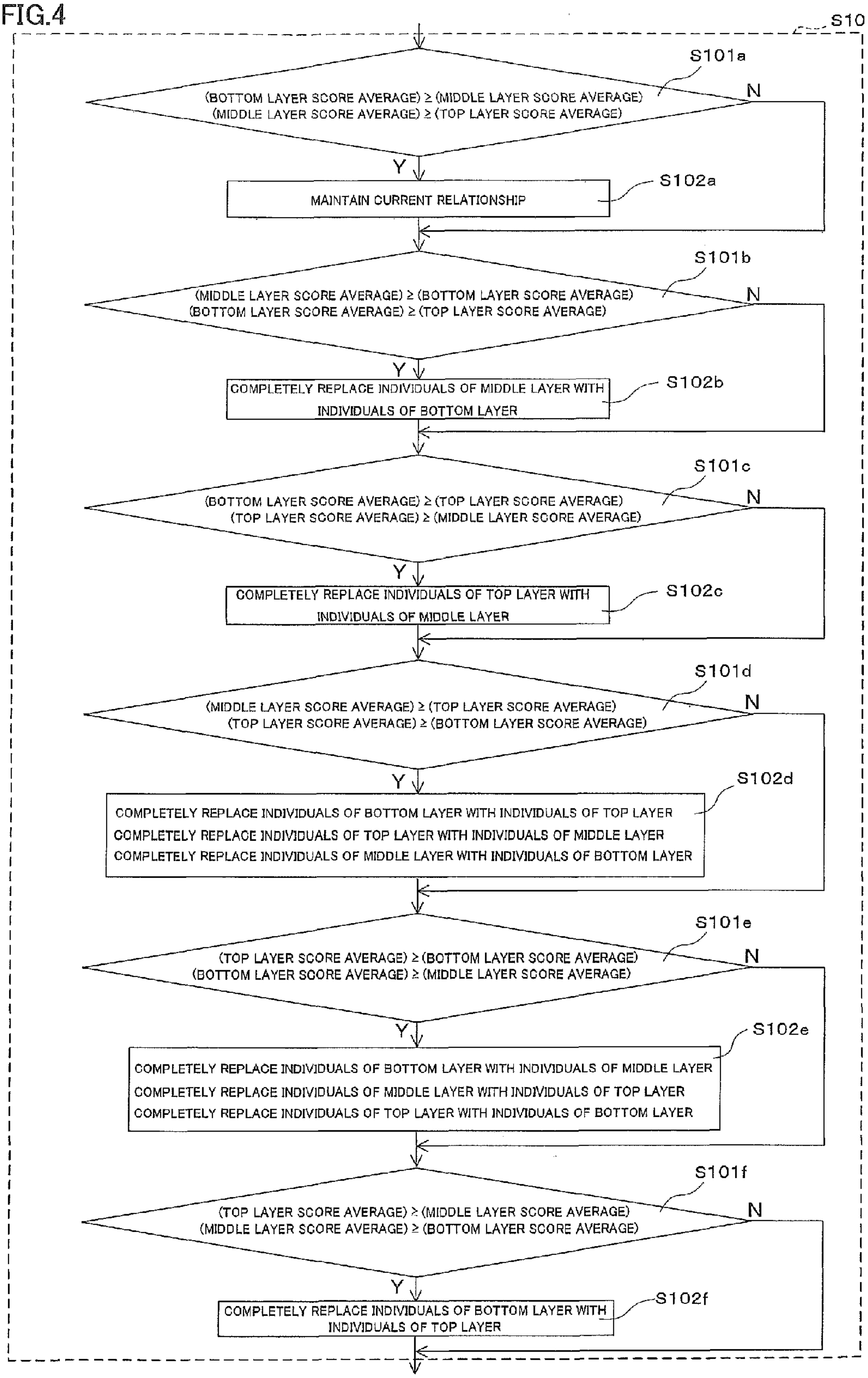
FIG.4
S10
S101a
(BOTTOM LAYER SCORE AVERAGE) ≥ (MIDDLE LAYER SCORE AVERAGE)
(MIDDLE LAYER SCORE AVERAGE) ≥ (TOP LAYER SCORE AVERAGE)
N
Y
MAINTAIN CURRENT RELATIONSHIP
S102a
S101b
(MIDDLE LAYER SCORE AVERAGE) ≥ (BOTTOM LAYER SCORE AVERAGE)
(BOTTOM LAYER SCORE AVERAGE) ≥ (TOP LAYER SCORE AVERAGE)
N
Y
COMPLETELY REPLACE INDIVIDUALS OF MIDDLE LAYER WITH INDIVIDUALS OF BOTTOM LAYER
S102b
S101c
(BOTTOM LAYER SCORE AVERAGE) ≥ (TOP LAYER SCORE AVERAGE)
(TOP LAYER SCORE AVERAGE) ≥ (MIDDLE LAYER SCORE AVERAGE)
N
Y
COMPLETELY REPLACE INDIVIDUALS OF TOP LAYER WITH INDIVIDUALS OF MIDDLE LAYER
S102c
S101d
(MIDDLE LAYER SCORE AVERAGE) ≥ (TOP LAYER SCORE AVERAGE)
(TOP LAYER SCORE AVERAGE) ≥ (BOTTOM LAYER SCORE AVERAGE)
N
Y
COMPLETELY REPLACE INDIVIDUALS OF BOTTOM LAYER WITH INDIVIDUALS OF TOP LAYER
COMPLETELY REPLACE INDIVIDUALS OF TOP LAYER WITH INDIVIDUALS OF MIDDLE LAYER
COMPLETELY REPLACE INDIVIDUALS OF MIDDLE LAYER WITH INDIVIDUALS OF BOTTOM LAYER
S102d
S101e
(TOP LAYER SCORE AVERAGE) ≥ (BOTTOM LAYER SCORE AVERAGE)
(BOTTOM LAYER SCORE AVERAGE) ≥ (MIDDLE LAYER SCORE AVERAGE)
N
Y
COMPLETELY REPLACE INDIVIDUALS OF BOTTOM LAYER WITH INDIVIDUALS OF MIDDLE LAYER
COMPLETELY REPLACE INDIVIDUALS OF MIDDLE LAYER WITH INDIVIDUALS OF TOP LAYER
COMPLETELY REPLACE INDIVIDUALS OF TOP LAYER WITH INDIVIDUALS OF BOTTOM LAYER
S102e
S101f
(TOP LAYER SCORE AVERAGE) ≥ (MIDDLE LAYER SCORE AVERAGE)
(MIDDLE LAYER SCORE AVERAGE) ≥ (BOTTOM LAYER SCORE AVERAGE)
N
Y
COMPLETELY REPLACE INDIVIDUALS OF BOTTOM LAYER WITH INDIVIDUALS OF TOP LAYER
S102f

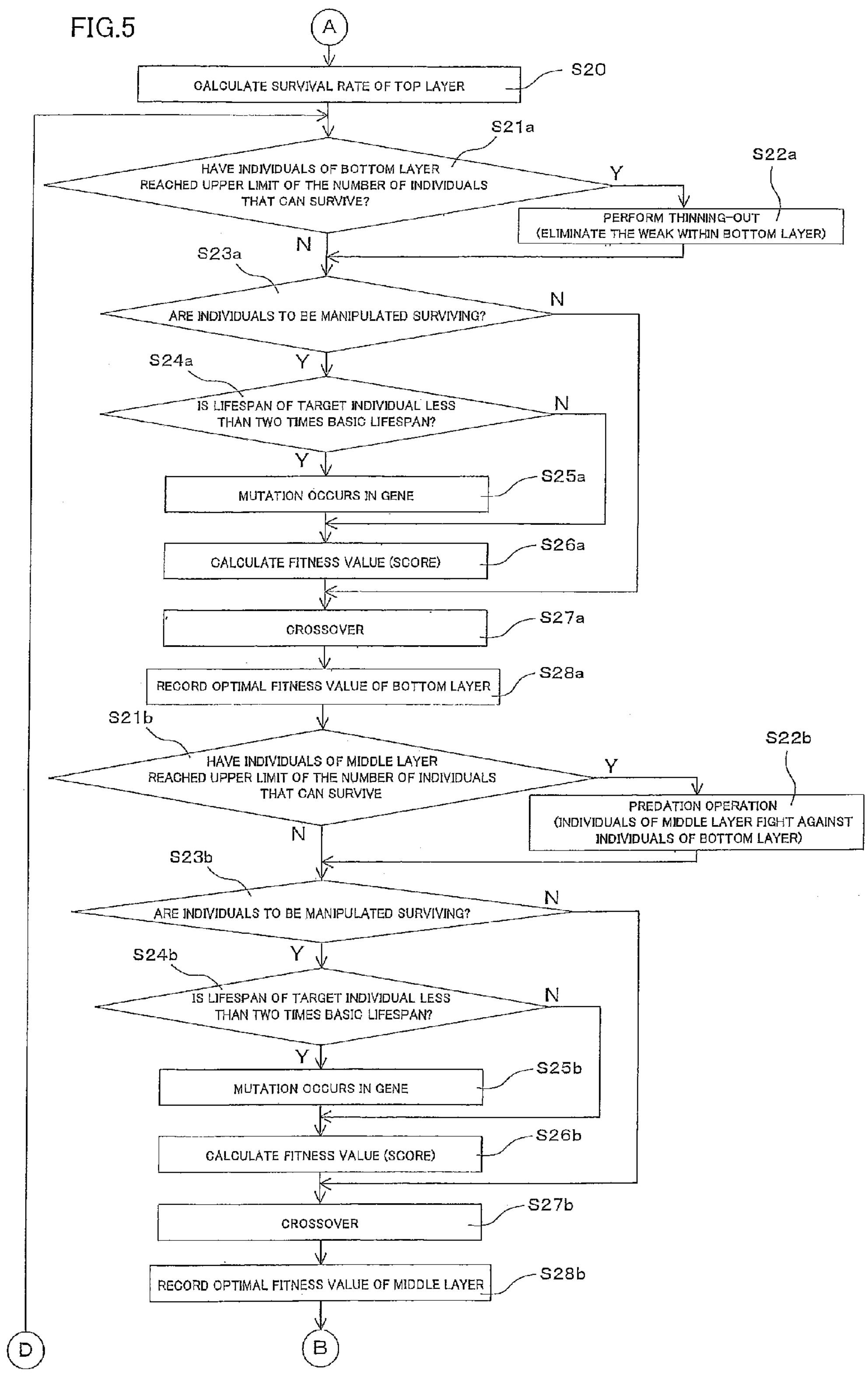

FIG.5
A
CALCULATE SURVIVAL RATE OF TOP LAYER
S20
S21a
HAVE INDIVIDUALS OF BOTTOM LAYER REACHED UPPER LIMIT OF THE NUMBER OF INDIVIDUALS THAT CAN SURVIVE?
Y
S22a
PERFORM THINNING-OUT (ELIMINATE THE WEAK WITHIN BOTTOM LAYER)
N
S23a
ARE INDIVIDUALS TO BE MANIPULATED SURVIVING?
N
Y
S24a
IS LIFESPAN OF TARGET INDIVIDUAL LESS THAN TWO TIMES BASIC LIFESPAN?
N
Y
MUTATION OCCURS IN GENE
S25a
CALCULATE FITNESS VALUE (SCORE)
S26a
CROSSOVER
S27a
RECORD OPTIMAL FITNESS VALUE OF BOTTOM LAYER
S28a
S21b
HAVE INDIVIDUALS OF MIDDLE LAYER REACHED UPPER LIMIT OF THE NUMBER OF INDIVIDUALS THAT CAN SURVIVE
Y
S22b
PREDATION OPERATION (INDIVIDUALS OF MIDDLE LAYER FIGHT AGAINST INDIVIDUALS OF BOTTOM LAYER)
N
S23b
ARE INDIVIDUALS TO BE MANIPULATED SURVIVING?
N
Y
S24b
IS LIFESPAN OF TARGET INDIVIDUAL LESS THAN TWO TIMES BASIC LIFESPAN?
N
Y
MUTATION OCCURS IN GENE
S25b
CALCULATE FITNESS VALUE (SCORE)
S26b
CROSSOVER
S27b
RECORD OPTIMAL FITNESS VALUE OF MIDDLE LAYER
S28b
D
B

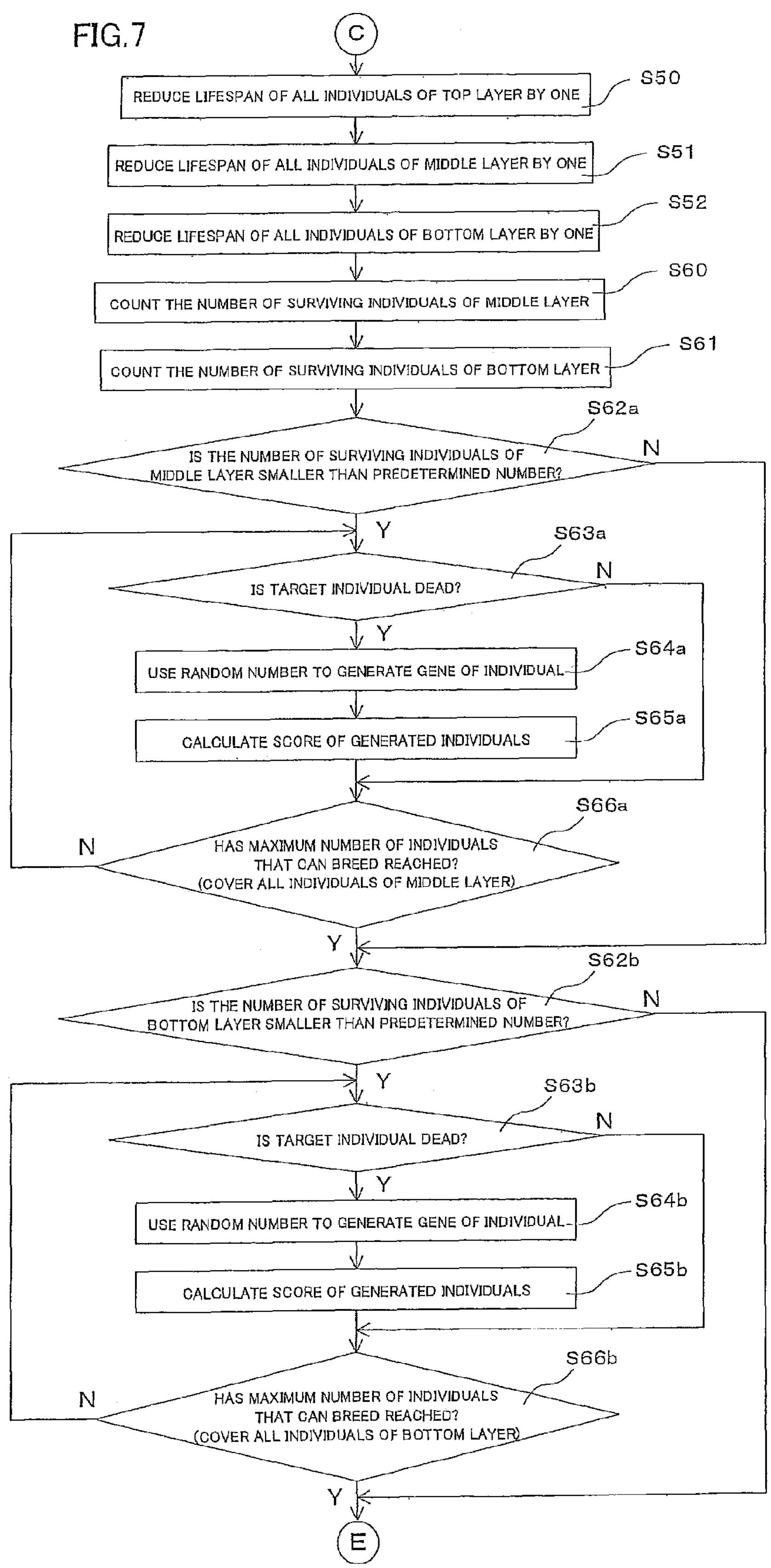
FIG.7
C
REDUCE LIFESPAN OF ALL INDIVIDUALS OF TOP LAYER BY ONE
S50
REDUCE LIFESPAN OF ALL INDIVIDUALS OF MIDDLE LAYER BY ONE
S51
REDUCE LIFESPAN OF ALL INDIVIDUALS OF BOTTOM LAYER BY ONE
S52
COUNT THE NUMBER OF SURVIVING INDIVIDUALS OF MIDDLE LAYER
S60
COUNT THE NUMBER OF SURVIVING INDIVIDUALS OF BOTTOM LAYER
S61
S62a
IS THE NUMBER OF SURVIVING INDIVIDUALS OF MIDDLE LAYER SMALLER THAN PREDETERMINED NUMBER?
N
Y
S63a
IS TARGET INDIVIDUAL DEAD?
N
Y
USE RANDOM NUMBER TO GENERATE GENE OF INDIVIDUAL
S64a
CALCULATE SCORE OF GENERATED INDIVIDUALS
S65a
S66a
HAS MAXIMUM NUMBER OF INDIVIDUALS THAT CAN BREED REACHED? (COVER ALL INDIVIDUALS OF MIDDLE LAYER)
N
Y
S62b
IS THE NUMBER OF SURVIVING INDIVIDUALS OF BOTTOM LAYER SMALLER THAN PREDETERMINED NUMBER?
N
Y
S63b
IS TARGET INDIVIDUAL DEAD?
N
Y
USE RANDOM NUMBER TO GENERATE GENE OF INDIVIDUAL
S64b
CALCULATE SCORE OF GENERATED INDIVIDUALS
S65b
S66b
HAS MAXIMUM NUMBER OF INDIVIDUALS THAT CAN BREED REACHED? (COVER ALL INDIVIDUALS OF BOTTOM LAYER)
N
Y
E FIG.9A
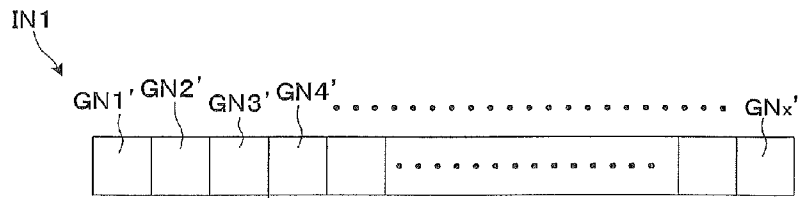
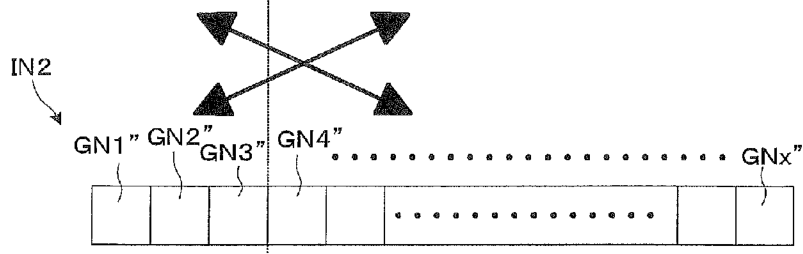
FIG.9B
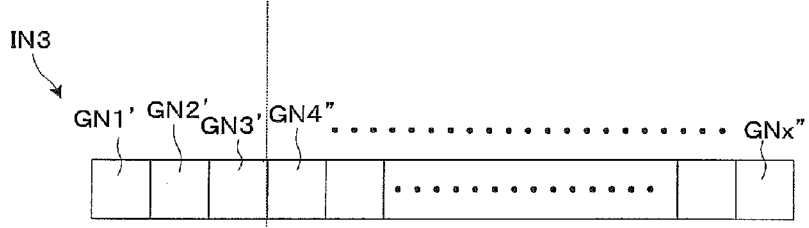
FIG.9C
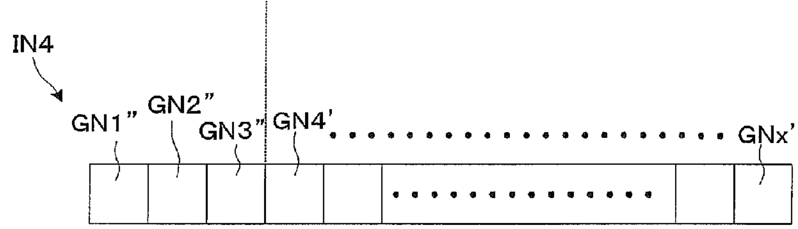
FIG.9D
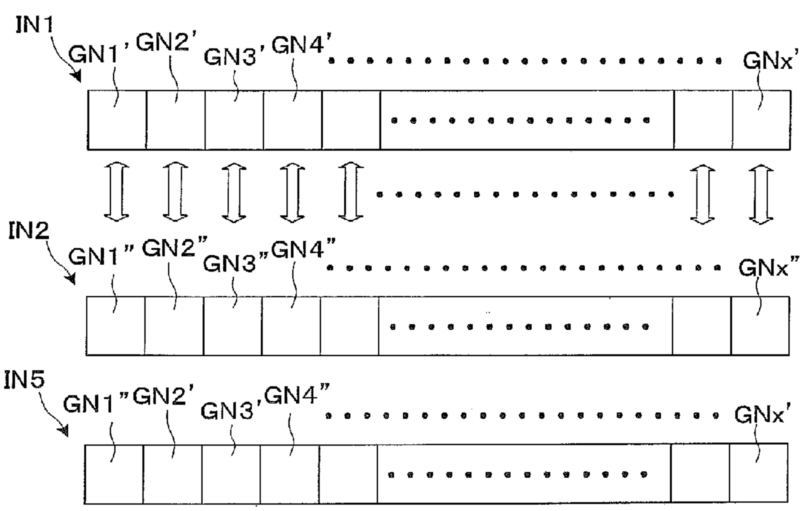
FIG.9E SCORE AVERAGE VALUE IN EACH LAYER IN GENERATION TRANSITION AND TRANSITION OF OPTIMAL FITNESS VALUE IN EACH LAYER
Score
Q1
Q2
Q3
C1
C2
C3
TOP_top
MID_top
BOT_top
TOP_ave
MID_ave
BOT_ave

OPTIMAL SOLUTION SEARCH METHOD AND OPTIMAL SOLUTION SEARCH DEVICE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 C.F.R. 1.57.

CROSS-REFERENCE TO RELATED APPLICATIONS

This application is the National Stage of International Application No. PCT/JP2012/075974, entitled Optimal Solution Search Method and Optimal Solution Search Device, filed on Oct. 5, 2012, which claims the benefit of priority to Japanese Patent Application No. 2011-223215 filed on Oct. 7, 2011. The disclosures of the above-described applications are hereby expressly incorporated by reference in their entireties.

TECHNICAL FIELD

The present invention relates to a search method of a pertinent solution and a pertinent solution search device that search for a solution considered to be appropriate, from candidate elements of solutions of a problem for finding an efficient processing of a case, for example.

BACKGROUND ART

The use of a neural network (hereinafter, referred to as NN) is generally known as one of the methods of searching for the optimum solution to a set problem. The NN is a network in which models of plural brain cells are arranged, and which is used to find the optimum solution.

Furthermore, several examples of the use of a genetic algorithm (hereinafter, referred to as general GA) are known as another method (for example, see Non Patent Literatures 1 and 2 etc.). General GA is a type of evolutionary computation in which the target of the problem is expressed in the form of a gene, and it makes the gene to be evolved through mating and mutation. General GA is an algorithm that is built on the basis of Darwin's theory of evolution.

However, according to NN, the search method is a linear type steepest descent method, and strongly depends on the search start position, therefore it brings a defect that it converges on a minimum point in the value around the search start position and never getting to the optimum solution or a nearby value in many cases, which is so-called local minimum.

Furthermore, according to the general GA described in the above Non Patent Literature 1 etc., it tends to converge on one specific species only, and It cannot be made to evolve to the optimum solution in many cases, although the situation is different from NN, the problem of local minimum is seen. That is, the types of genes become less in the process of evolution, and convergence occurs on solutions that are far away from the optimum solution and rather than the optimum solution. Furthermore, according to the general GA, when a problem is searched and the solution is found out, the information of a gene, that is, an individual, is biased thus leading to an oligopoly situation where there is no diversity of species. As a result, the gene cluster cannot be applied as is to another problem. Therefore, when dealing with another problem, it becomes necessary to perform reinitialization in order to solve the problem. Thus, for example, if the characteristics of a problem for which an optimum solution is to be found out time series change, the problem cannot be handled promptly.

CITATION LIST

Patent Literature

[NPL 1] Journal of Information Processing Society of Japan: Mathematical Modeling and Its Applications Neighborhood Cultivation Genetic Algorithm for Multi-Objective Optimization Problems pp. 183-198, November 2002

[NPL 2] Journal of Information Processing Society of Japan: Mathematical Modeling and Its Applications Effectiveness of Neighborhood Crossover in EMO Algorithms pp. 40-48, February 2007

SUMMARY OF INVENTION

The purpose of the present invention is to provide a search method of a pertinent solution and a pertinent solution search device that avoid being trapped into a local minimum, and are capable of coping with a problem involving a time series change flexibly.

In order to resolve the above-described problem, a search method of a pertinent solution according to the present invention is using a genetic algorithm that performs genetic operation including selection, mutation, and crossover of a plurality of individuals each having an element of the candidate solution to a problem in the form of a gene sequence, comprising: (a) an initial individual generating step of generating a plurality of initial individuals and using the plurality of initial individuals as a plurality of target individuals that are the target of processing; (b) an information storing step of storing, in an information storage portion, the genetic information about the plurality of target individuals generated in the initial individual generating step; (c) a genetic operation step of generating a plurality of new target individuals from the plurality of existing target individuals by performing at least one genetic operation among selection, mutation, and crossover for at least one of the plurality of target individuals; (d) an information writing step of writing, to the information storage portion, the genetic information about the plurality of new target individuals generated in the genetic operation step; (e) an fitness value calculation step of calculating an fitness value corresponding to the candidate solution to the problem on the basis of the gene sequence of each of the plurality of initial individuals and the plurality of new target individuals; (f) a reprocessing step of repeating the genetic operation step and the fitness value calculation step for the plurality of new target individuals; and (g) a candidate solution extraction step of setting at least one value with the highest adaptability among plural fitness values obtained in the fitness value calculation step that is repeated plural times, as one of the candidate solutions to the problem, wherein (h) the information storage portion includes, as one of the items of the genetic information about the plurality of target individuals, the information about whether an each individual is in which state among the living state that is the target of genetic operation in the genetic operation step and the target of the calculation of the fitness value in the fitness value calculation step, and the dead state that is not the target of genetic operation nor the target of the calculation of the fitness value.

An individual is a representation of an element of the candidate solution to a problem in the form of a gene sequence. Furthermore, in addition to information on the living state or dead state of each individual, the genetic information of a plurality of individuals includes various types of information concerning each individual, such as the gene sequence of each individual, and the fitness value calculated from the gene sequence. Furthermore, a gene sequence implies modeling of the chromosomes of a gene in the living world, and this gene order acts as an element of the candidate solution to a problem. The solution to a problem includes a plurality of elements, and is evaluated based on the dominance (superiority) of the fitness values of a plurality of individuals. Furthermore, as regard genetic operation, selection refers to modeling of natural selection in the living world according to which among a plurality of individuals, those that are well adapted to the environment, for example, continue to survive, on the other hand, the others perish, and is a operation by which based on genetic information such as fitness values, among a plurality of individuals, those that satisfy the conditions remain behind and those that do not are eliminated. Mutation refers to modeling of mutations of genes in the living world, and is a process by which a part of the gene sequence of an individual is changed. Crossover refers to modeling of the fact that living organisms produce offspring by mating, and is a process by which a part of the gene sequence is replaced mutually among a plurality of individuals.

According to the above-described search method of a pertinent solution, the information about the living state and the dead state is included as one of the genetic information items regarding a plurality of individuals. Thus, even if an individual has a relatively good fitness value (adaptability), or an fitness value (adaptability) that is not good, each individual is finally culled out (selected) by meeting death. Thus, for example, the creation of an oligopoly situation by individuals having an fitness value that is relatively good but not to the extent of a pertinent solution is not seen, and the issue of being led to a local minimum while searching for a pertinent solution to the set problem is avoided. Furthermore, individuals that have a good fitness value as well as those that do not have a good fitness value undergo life and death, because of which diversification of the information of an individual can be realized, and after searching for the solution to a problem, if each parameter, for example, is modified for setting a new problem, the solution to the new problem can be searched without making the initial settings for the individual again, and thus even problems that time series change can be handled.

According to a specific aspect or viewpoint of the present invention, each of a plurality of target individuals has a predetermined value of lifespan, and the invention further includes a generation updating step of updating a generation of the plurality of target individuals in correspond to the genetic operation step, and reducing the lifespan. In such a case, every individual has a lifespan, and the lifespan reduces by one in each generation. Once the lifespan is over, an individual reaches its death regardless of the dominance of the fitness value, and crossover and mutation cannot be performed for a dead individual. Thus, the fact that only individuals having a specific biased gene continue to live can be avoided, and diversification of the information of an individual can be achieved.

According to another aspect of the present invention, the lifespan of a plurality of target individuals differs among individuals depending on the fitness value of each individual. In such a case, for example, the lifespan of an individual having a relatively good fitness value can be relatively lengthened and set to a favorable state. Thus, due to the fact that all individuals have a lifespan, individuals having a relatively good gene sequence can be retained preferentially while securing the diversity of individuals as a whole, which enables a relatively quick search of the candidate solution to a problem.

According to yet another aspect of the present invention, in an initial individual generating step and a genetic operation step, a single or a plurality of breeding areas, where a plurality of target individuals can be retained up to a predetermined number, are provided. In such a case, a plurality of individuals can be retained in a breeding area. Particularly, by providing a plurality of breeding areas and classifying and handling a plurality of individuals in different layers, it becomes possible to construct a search system that applies a natural food chain.

According to yet another aspect of the present invention, a breeding area is composed of a plurality of layers, and the plurality of layers have a relatively high and low ranking, and a predation step of leading an individual belonging to a lower layer to a dead state due to predation by an individual belonging to a higher layer in the breeding area constitutes an aspect of a genetic operation step. In such a case, it is possible to construct a search system that applies a natural relationship where a predator and a prey, in other words, a side that eats and a side that is eaten, exist on the basis of the predation step.

According to yet another aspect of the present invention, individuals belonging to different layers in a breeding area do not cross over, and crossover occurs only between individuals belonging to the same layer. In such a case, the natural condition in which crossover occurs only between limited species can be applied. By applying the natural condition that aims at continuation of life by adapting to the environment, it is possible to approach quickly to a pertinent solution that must be found out.

According to yet another aspect of the present invention, in the predation step, when one individual of a higher layer is successful in predation of one individual of a lower layer, the individual of the lower layer that is preyed upon reaches the dead state, and in the case of failure in predation, the individual of the higher layer that has failed in predation reaches the dead state. In such a case, in the predation step, the number of individuals in the lower layer declines by being preyed upon, and the number of individuals in the higher layer declines by being not possible to prey, and thus, the natural condition of making the difference between life and death on the basis of the success and failure in predation is applied.

According to yet another aspect of the present invention, in the predation step, the success or failure in predation is determined by the adaptability of the fitness value of each individual. In such a case, for example, an individual with a higher adaptability becomes the winner and the loser becomes the prey, which means that the natural condition is applied.

According to yet another aspect of the present invention, in the breeding area, when the number of individuals belonging to a layer has reduced below a predetermined survivable limit, an extinction avoiding step of increasing the number of individuals belonging to the layer up to a predetermined viable number is further included. In such a case, the number of individuals belonging to the layer and the diversity can be maintained, and furthermore, this results in modeling of a natural biological explosion.

According to yet another aspect of the present invention, a successive-generation fitness value recording step of recording all fitness values obtained by repeating an fitness value calculation step in an information storage portion is further included, and among all the fitness values recorded in the successive-generation fitness value recording step, the value with the highest adaptability is the candidate solution to the problem. In such a case, the fitness value considered to be the most suitable among the individuals having diversity can be selected as the candidate solution to the problem.

According to yet another aspect of the present invention, a layer exchange step of completely replacing the individuals belonging to one layer with individuals belonging to another layer with reference to an average value of the fitness values of individuals belonging to a plurality of layers constituting a breeding area is further included. In such a case, a radical phenomenon of role reversal of the side that eats and the side that is eaten is incorporated. Such a radical phenomenon that can be seen in nature as well has been applied in the present invention.

According to yet another aspect of the present invention, a new search setting step of setting a new problem after determining the candidate solution to a problem, as well as using the plurality of target individuals at the time of determining the previous candidate solution as the plurality of initial individuals generated by the initial individual generating step is further included. In such a case, in situations where the characteristics of a problem time series change, such as when the solution to a new problem is to be searched after searching for the candidate solution to one problem, the new problem can be handled without making the initial settings for a plurality of individuals, again.

According to yet another aspect of the present invention, each of a plurality of target individuals has a female or a male gender, and the genetic operation step includes male selection. Male selection refers to modeling of the phenomenon of directing the genes of males to suit the preferences of females in nature, for example. In such a case, for example, a battle for survival is initiated by comparing the fitness values between male individuals among the target individuals such that modeling of male selection seen in nature is enabled.

In order to resolve the above-described problem, a pertinent solution search device according to the present invention using a genetic algorithm that performs genetic operation including selection, mutation, and crossover of a plurality of individuals each having an element of the candidate solution to a problem in the form of a gene sequence, comprising: (a) an initial individual generating portion that generates a plurality of initial individuals and uses the plurality of initial individuals as a plurality of target individuals that are the target of processing; (b) an information storage portion that stores genetic information about the plurality of target individuals; (c) a genetic operation portion that generates a plurality of new target individuals from the plurality of existing target individuals by performing at least one genetic operation among selection, mutation, and crossover for at least one of the plurality of target individuals; (d) an information writing portion that writes, to the information storage portion, the genetic information about the plurality of new target individuals generated by the genetic operation portion; (e) an fitness value calculation portion that calculates an fitness value corresponding to the candidate solution to the problem on the basis of the gene sequence of each of the plurality of initial individuals and the plurality of new target individuals; (f) a reprocessing portion that repeats the processing performed by the genetic operation portion and the fitness value calculation portion for the plurality of new target individuals; and (g) a candidate solution storage portion that stores at least one value with the highest adaptability among the plural fitness values obtained in the fitness value calculation portion by repeating the processing plural times, as one of the candidate solutions to the problem, wherein (h) the information storage portion includes, as one of the items of the genetic information about the plurality of target individuals, the information about whether an each individual is in which state among the living state that is the target of genetic operation in the genetic operation portion and the target of the calculation of the fitness value in the fitness value calculation portion, and the dead state that is not the target of genetic operation nor the target of the calculation of the fitness value.

According to the above-described pertinent solution search device, the information about the living state and the dead state is included as one of the genetic information items regarding a plurality of individuals. Thus, even if an individual has a relatively good fitness value (adaptability), or an fitness value (adaptability) that is not good, each individual is finally culled out (selected) by meeting death. Thus, for example, the creation of an oligopoly situation by individuals having an fitness value that is relatively good but not to the extent of a pertinent solution is not seen, and the issue of being led to a local minimum is avoided. Furthermore, individuals that have a good fitness value as well as those that do not have a good fitness value undergo life and death, because of which diversification of the information of an individual can be realized, and even problems that time series change, such as when the solution to a new problem is to be searched after searching for the solution to one problem, can be handled.

BRIEF DESCRIPTION OF DRAWINGS

FIG. 2 is a diagram that conceptually illustrates a memory map in a storage device.

FIG. 3 is a flowchart that conceptually explains a search method of a pertinent solution using the pertinent solution search device of FIG. 1.

FIG. 4 is a flowchart that conceptually explains a step of layer exchange in the search method of a pertinent solution shown in FIG. 3.

FIG. 5 is a flowchart that conceptually explains a search method of a pertinent solution using the pertinent solution search device of FIG. 1.

FIG. 7 is a flowchart that conceptually explains a search method of a pertinent solution using the pertinent solution search device of FIG. 1.

FIG. 9A through FIG. 9D are diagrams for explaining crossover by a first method, and FIG. 9E is a diagram for explaining crossover by a second method.

DESCRIPTION OF EMBODIMENTS

First Embodiment

Hereinafter, a search method of a pertinent solution and a pertinent solution search device according to a first embodiment of the present invention will be described with reference to drawings.

Figure 1A:
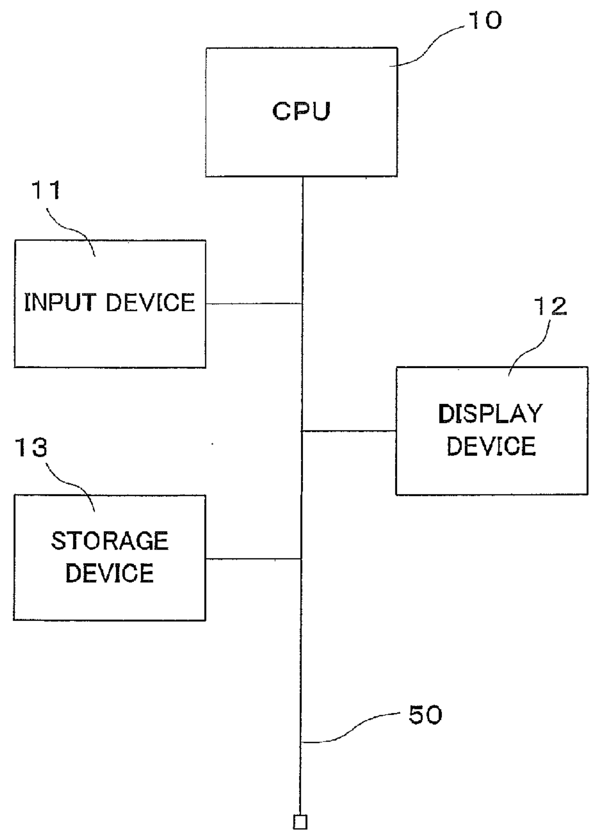
FIG. 1A is a block diagram that conceptually explains a structure of a pertinent solution search device according to a first embodiment.

As illustrated in FIG. 1A, the pertinent solution search device 100 according to the present embodiment includes a CPU 10, an input device 11, a display device 12, a storage device 13, and a bus 50, same as a general computer.

The CPU 10 is capable of transferring data mutually among the input device 11, the display device 12, and the storage device 13 via the bus 50. Furthermore, on the basis of an instruction of an operator from the input device 11, the CPU 10 reads a predetermined program and data from the storage device 13, and performs various types of processing based on the program and data.

Specifically speaking, in a search program for a pertinent solution, as regard the problems input to the storage device 13 and the like, the CPU 10 can search and output the candidate solution to a set problem by a genetic algorithm on the basis of an instruction from the input device 11.

The input device 11 is configured by a keyboard, a printer and the like, and outputs an instruction signal reflecting the intention of the operator operating the pertinent solution search device 100 to the CPU 10, and, for example, prints out the information constituting the processing result based on the instruction from the CPU 10 in an appropriate format.

The display device 12 performs the necessary display on the basis of an instruction signal from the CPU 10 and is configured by a display drive circuit that generates a drive signal on the basis of the data input from the CPU 10, and an image display portion (or unit) that performs the necessary display on the basis of the drive signal input from the display drive circuit.

Figure 1B:
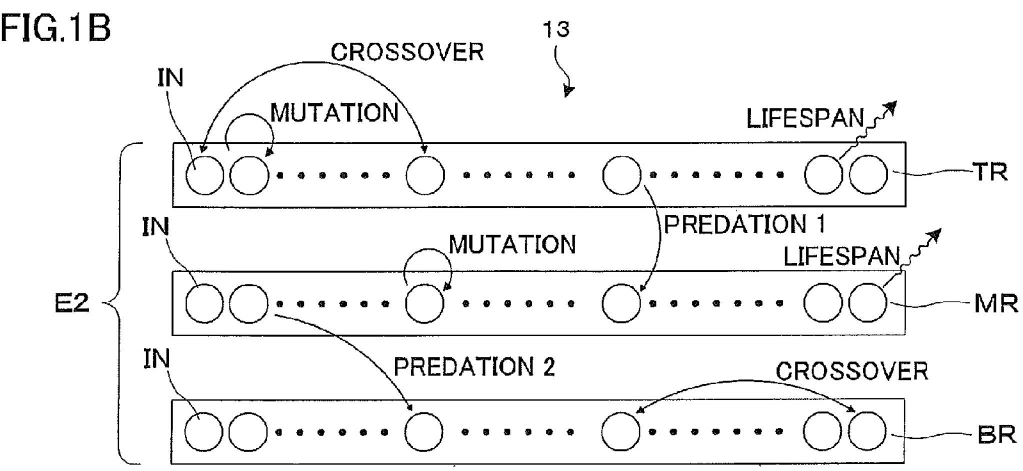
FIG. 1B is a diagram that conceptually illustrates a condition of information management of a plurality of individuals.
Figure 1C:
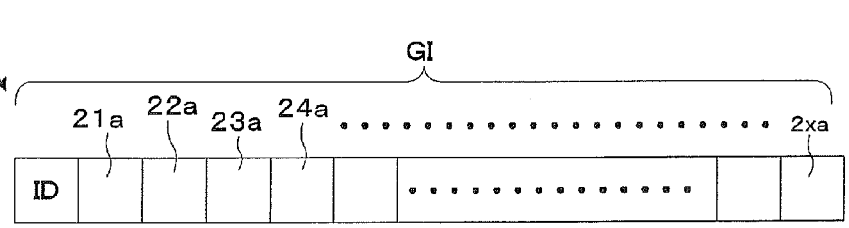
FIG. 1C is a diagram that conceptually illustrates the information included in one individual.
Figure 6:
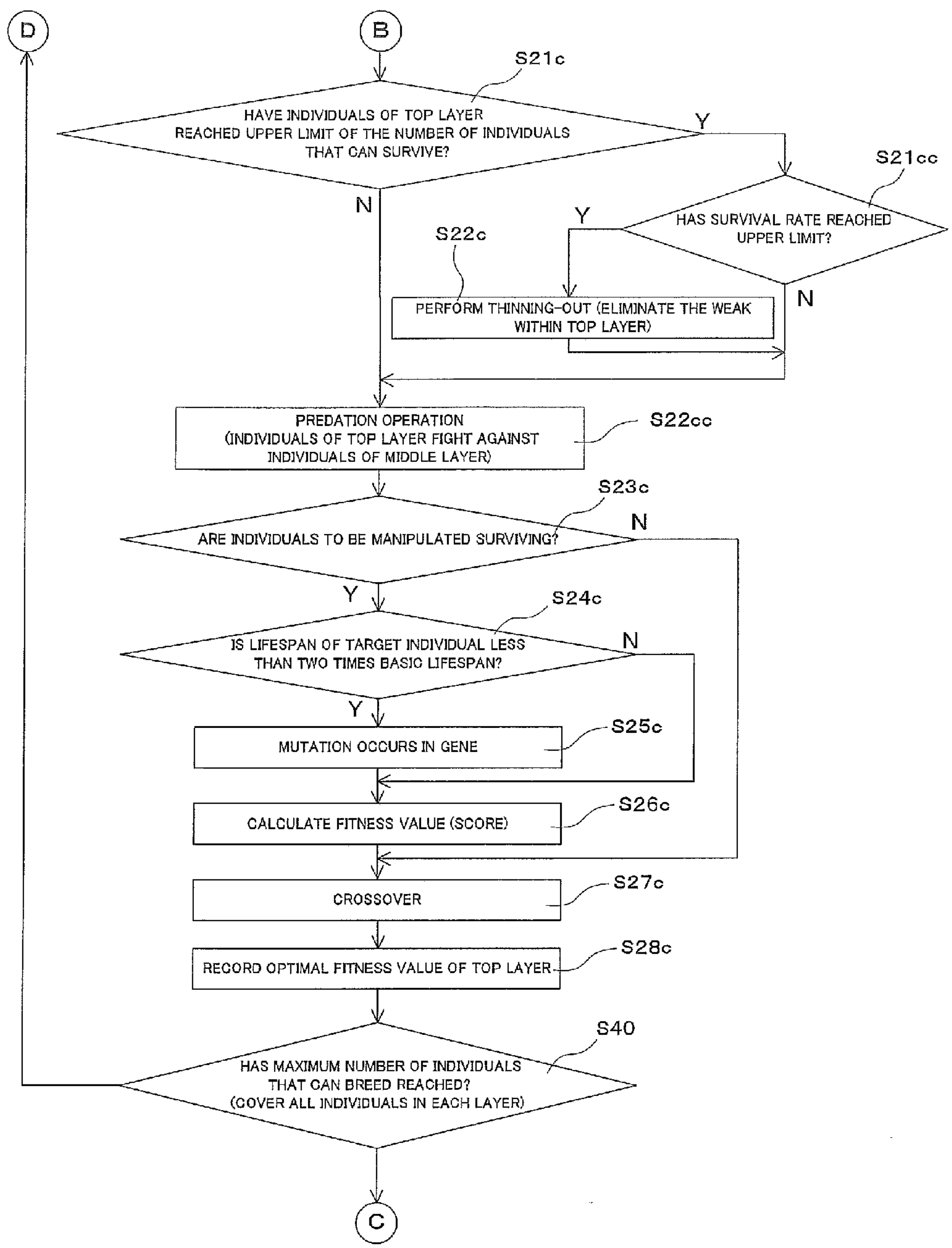
FIG. 6 is a flowchart that conceptually explains a search method of a pertinent solution using the pertinent solution search device of FIG. 1.
Figure 8:
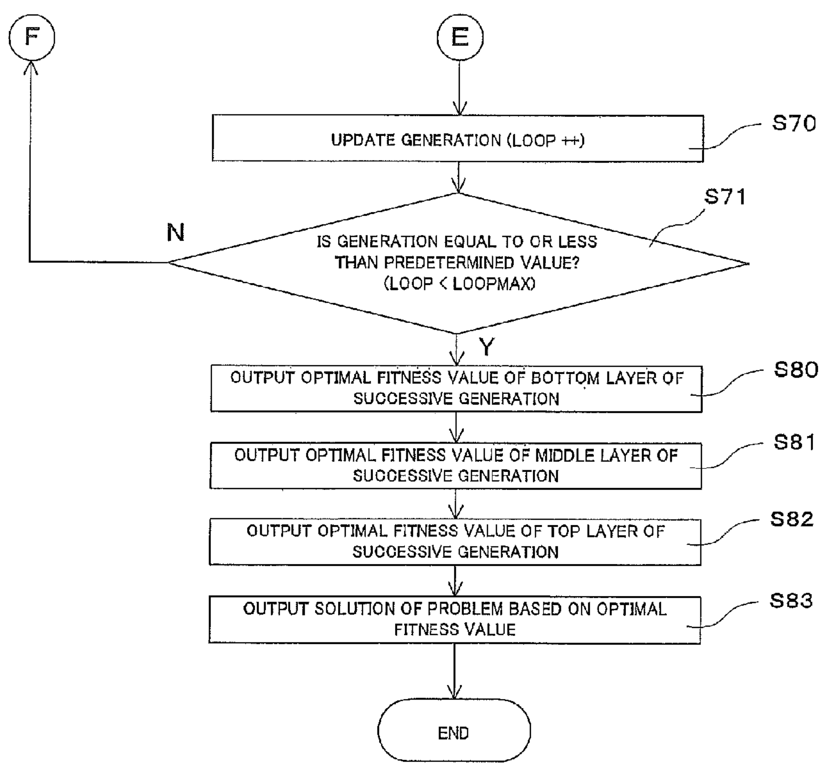
FIG. 8 is a flowchart that conceptually explains a search method of a pertinent solution using the pertinent solution search device of FIG. 1.

The storage device 13 includes a program region in which various types of programs for operating the pertinent solution search device 100 are stored, and a data region in which the input instructions, the input data, the processing result and the like are stored temporarily. The storage device 13 functions as an information storage portion (unit) that stores various types of information, such as each parameter for securing adaptability of a problem, which is set as a subject, to enable search by the pertinent solution search device 100, and the genetic information of multiple (or plural) individuals having a gene sequence that is provided for searching for a solution to the set problem, and that stores a program that is appropriately rewritten in accordance with a program for performing a genetic operation step, such as crossover and mutation and the like, for various types of information of multiple individuals IN shown in FIG. 1B. Particularly, in the present embodiment, as illustrated in FIG. 1C, in addition to self-ID, the individual IN includes, in an area 21*a*, the information about whether each individual is in among a dead state and a living state, as one of the genetic information GI constituting the sequence information of a gene sequence. The living state is the target of genetic operation in the genetic operation step, and the target of calculation of the fitness value, while the dead state is neither the target of genetic operation in the genetic operation step, nor the target of calculation of the fitness value. That is, in the present embodiment, by adopting a configuration in which each individual IN is a target of the pertinent solution search only in the living state, and moves away from the target in the dead state someday, the diversity of individuals is secured, and a pertinent solution can be derived at in a relatively faster time, which was not seen in the conventional general GA.

Next, a problem that is set as the subject to be searched by a program for a pertinent solution search will be described. In the present embodiment, TSP (traveling salesman problem) is addressed as an example. That is, the parameters that must be input for the set problem are the number of cities in TCP and the distance between cities, and the purpose (goal) is to find the shortest path when traveling across all cities. In the present embodiment, in multiple individuals each having a respective gene sequence, the number of gene sequences that are common to all individuals corresponds to the number of cities, and the gene order of each individual corresponds to the order of traveling around the city. Furthermore, the length of the path when traveling in each order is the fitness value of each individual. Therefore, in the case of the above settings, an individual with a smaller fitness value has a higher adaptability. Furthermore, in this case, the explanation is focused on TSP as described above, however, the problems which are subject to general GA are not limited to TSP but include various types, and therefore, by using the search method of a pertinent solution by using the pertinent solution search device 100 of the present embodiment, various types of problems can be handled.

FIG. 2 illustrates a memory map of the various types of data and programs that are stored in the storage device 13 in the pertinent solution search device 100. That is, when performing various types of operations, the CPU 10 appropriately reads and executes the necessary data and various types of programs from the storage device 13.

First of all, in FIG. 2, the storage device 13 includes a data region D1 for storing various types of data, and a program region D2 for storing various types of programs. The data region D1 includes an initial data storage region E1 that stores the initial information including the conditions set in the problem, an individual data storage region E2 that stores various types of information about an individual, and a generations counter E3 for counting the number of generations that increases with a generation update. Furthermore, the program region D2 includes an initial setting control portion (unit) P1 that is a set of programs for processing the initial information, a fitness value (score) calculation portion (unit) P2 that is a program for calculating the fitness value of each individual, and a genetic operation control portion (unit) P3 that is a set of programs for performing various operations in a genetic algorithm. In the present embodiment, as illustrated in FIG. 1B and FIG. 2, as an example, relatively ranked three layers (or classes) including a top layer TR that is the highest layer (or class), a middle layer MR that is the middle layer (class), and a bottom layer BR that is the lowest layer (class) are provided in the individual data storage region E2 as the breeding area to which each individual IN belongs. As illustrated in FIG. 1B, each time a mutation in each individual IN, a crossover between the individuals IN within each layer, or the process of a predation 1 or a predation 2 that is predation of an individual IN in a lower side by an individual IN in an upper layer is performed, the content of the individual data storage region E2 is rewritten. In each layer of TR, MR, and BR, for example, up to 50 individuals IN can be retained, respectively. By preparing multiple breeding areas, the relationship of a food chain is mimicked and applied. Furthermore, in the present embodiment, due to the existence of the relationship of a prey and a predator among layers, co-evolution is progressed. The method of searching for a solution by using such a mechanism is called Co-evolution Diversity Solution (CDS).

In the data region D1, first of all, the initial data storage region E1 is the data region for storing data about each variable which determined by the initial settings, such as the number of gene sequences of an individual, which is an input parameter for the set problem (here, TSP), and for storing data about the number of breeding areas as well as the number of individuals that can be retained in each breeding area.

Next, the individual data storage region E2 is the portion that stores information specific to each individual belonging to any one of the three layers TR, MR, and BR, as described above. The individual data storage region E2 includes a life-death information storage region E21 that stores information about the living state and death of each individual, a gene sequence storage region E22 that stores the gene sequence of each individual, a fitness value (score) information storage region E23 that stores the information about the fitness value (score) of each individual, a lifespan storage region E24 that stores the information about the lifespan of each individual, and an optimal fitness value storage region E2*x* that stores the information about the smallest fitness value that is the optimal fitness value of each layer. That is, each region E21 through E24 and E2*x* of the individual data storage region E2 is an aggregate of each information item 21*a* through 24*a* and 2*xa* of each individual IN illustrated in FIG. 1C.

Finally, the generations counter E3 counts the number of generations when the generation is updated. For all individuals, the lifespan reduces with a generation update. In other words, the lifespan, that is, the age, which is stored in the lifespan storage region E24 changes with a generation update, and an individual whose lifespan is over reaches the dead state. In this case, the lifespan of each individual varies according to the fitness value of each individual. More specifically, for example, as compared to the lifespan of a normal individual which is five years, that is, the dead state comes when the generation is updated five times, the lifespan of an individual having a relatively good fitness value, that is, having an fitness value below a prescribed lower limit is three times longer than that of a normal individual. That means the lifespan is 15 years. Conversely, the lifespan of an individual that does not have a good fitness value, that is, has an fitness value that is more than a prescribed upper limit, is two years, which is shorter than normal. It must be noted that a prescribed lower-limit value and the upper-limit value can be determined from the average value of the score, for example. That is, an individual having a score that is higher than the average value (an individual with a poor fitness value) is determined to have a short lifespan, and an individual having a score that is lower than the average value (an individual with a good fitness value) is determined to have a long lifespan.

In the program region D2, first of all, the initial setting control portion (unit) P1 is a region that includes various types of programs for receiving the initial data and making initial settings by saving the initial data in each data region. Therefore, the initial setting control portion P1 includes a problem reading portion (unit) P11 that is a program for reading problem data such as each parameter for securing adaptability of a problem such as the number of cities of TSP, in other words, the number of gene sequences of an individual that is input via the input device 11 by an operation performed by an operator, to the processing of the pertinent solution search device 100, an initial gene generating portion (unit) P12 that is a program for generating a plurality of initial individuals having the information of a gene sequence, a breeding area generating portion (unit) P13 that is a program for generating a breeding area on the basis of the information of the number of breeding areas that is input, and an individual transfer portion (unit) that transfers individuals to a breeding area P14, which is a program for correlating the plurality of individuals generated in the initial gene generating portion P12 and the breeding area generating portion P13 with the breeding area, in other words, a program for determining that an initial individual belongs to which breeding area.

Next, the fitness value calculation portion (unit) P2 is a region that includes a program for calculating the fitness value of each individual. The fitness value of an individual has a direct relationship in the search for a solution to a set problem, and is not only used to directly find the candidate solution, but also used various indexes as required. Therefore, the fitness value calculation portion P2 is appropriately read in various types of processes, as and when necessary. As described earlier, in the present embodiment, among multiple individuals, an individual having the smallest score has the best fitness value, however, for example, in each breeding area, in other words, in each layer of TR, MR, and BR, the individual having the best fitness value is searched for.

Finally, the genetic operation control portion (unit) P3 is a region that includes a program that is necessary for performing various operations such as changes in life or death and gene sequence of each individual, or changes in the lifespan, in other words, changes in the age. The genetic operation control portion P3 includes a thinning-out control portion (unit) P31 that is a program for performing thinning out in order to adjust the number of individuals in each breeding area, a mutation control portion (unit) P32 that is a program for performing mutation, in other words, replacement of gene sequences, a crossover control portion (unit) P33 that is a program for controlling crossover, a predation activity control portion (unit) P34 that is a program for controlling the predation activity, an extinction avoiding control portion (unit) P35 that is a program for avoiding extinction when the number of individuals in the lower layers MR and BR that are the sides being preyed upon among the layers TR, MR, and BR falls below the survivable limit, by increasing the number up to the viable number, a lifespan control portion (unit) P36 that is a program for controlling the lifespan of each individual, a generation update portion (unit) P37 that is a program for performing generation update, an fitness value (score) average calculation portion (unit) P38 that is a program for calculating an average value of fitness values (scores), and a layer exchange control portion (unit) P39 that determines whether or not to exchange a layer on the basis of the result calculated by the fitness value (score) average calculation portion P38. Regarding crossover by the crossover control portion P33, crossover is not performed between individuals belonging to different layers among the above-described three layers TR, MR, and BR that are the breeding areas, and crossover is performed only between individuals belonging to the same layer. An example of the survivable limit described above is setting to half the number of the entire number of individuals in each layer. Furthermore, an example of the viable number is setting to the number of individuals to 50. For example, in the case of a TSP simulator, it is desired to set to 58% or above of the number of cities of TSP, in other words, the number of gene sequences as the viable number.

In the present embodiment, as already described, in addition to the fact that every individual has a life-or-death, and a lifespan, there are several characteristics that were not seen in the conventional general GA. First of all, there is a characteristic point that includes the predation activity control portion P34, and a predation activity exists within individuals belonged to their layers. As described above, this leads a pertinent solution more quickly by progressing co-evolution, which is a characteristic of CDS, based on the relationship between eating and being eaten. Furthermore, secondly, there is a characteristic point that has the extinction avoiding control portion P35 that mimics, in other words, applies and is modeled on the state of biological explosion in which the individuals of a layer that have started to become extinct increase in number through a sudden explosion. This is like, so to speak, an invisible hand of God. This enables the preservation and diversification of a species. Thirdly, the present embodiment includes the layer exchange control portion P39 that enables a radical phenomenon (Class Change) through the occurrence of a complete replacement of individuals by role reversal of each layer of TR, MR, and BR. This, for example, is an imitation of the changes seen even in nature that are occurring in accordance with the environmental changes where the bear that is originally a carnivore has evolved into an omnivore, and the panda, which is a type of bear, has become a herbivore feeding only on bamboo grass as its staple food.

Hereinafter, the main operation of the search method of a pertinent solution using the pertinent solution search device 100 illustrated in FIG. 1A is described. FIG. 3 through FIG. 8 are flowcharts for explaining, in an abstract form, a program for searching for a pertinent solution. A system that performs the operations described below can implement the program in, for example, a high-level language (such as C language, C++ language, and Java (registered trademark)).

First of all, the CPU 10 reads the program of the problem reading portion (unit) P11 from the initial setting control portion P1 of the program region D2, and then acquires each parameter, which is the problem data, via the input device 11 and the like, and secures adaptability of the problem, such as TSP, so as to enable processing by the pertinent solution search device 100, and at the same time, stores the problem data in the initial data storage region E1 of the storage device 13 (step S1).

Next, the CPU 10 reads the program of the initial gene generating portion P12, which is the initial individual generating portion, from the initial setting control portion P1, creates gene sequences of a plurality of initial individuals by using a random number, and stores the initial individual data in the initial data storage region E1 (step S2: Initial individual generating step).

Next, the CPU 10 reads the fitness value calculation portion P2, calculates the score, that is, the fitness value of each individual on the basis of the data of the gene sequence of each individual that is stored in the initial data storage region E1, for the initial individuals (step S3), and sorts each individual on the basis of the score, and at the same time, stores various types of information of each individual in the initial data storage region E1 (step S4: Information storing step). Next, the CPU 10 reads the breeding area generating portion P13 and the individual transfer portion that transfers individual to a breeding area P14, from the initial setting control portion P1, and then enters the initial value in each layer of TR, MR, and BR by assigning the sorted individuals in each breeding area allocated on the individual data storage region E2, that is, the three layers, namely the top layer TR constituting the highest layer, the middle layer MR constituting the middle layer, and the bottom layer BR constituting the lowest layer (step S5). Specifically, for example, in each layer of TR, MR, and BR that has been assigned, each generated individual is stored as a living state in the life-death information storage region E21, in terms of the living state and dead state, the gene order of the gene sequence is stored in the gene sequence storage region E22, the fitness value is stored in the fitness value (score) information storage region E23, and the lifespan is stored in the lifespan (age) storage region E24 as two years, five years, and 15 years. As a result of the above settings, the multiple initial individuals that are generated are handled as the multiple target individuals that are the target of the processing thereafter. Furthermore, as an example, in the initial target individuals, the individuals occupying the top 20% of the score belong to the top layer TR, the individuals occupying the middle 30% belong to the middle layer MR, and the individuals occupying the bottom 50% belong to the bottom layer BR. For example, if the number of individuals generated initially is 100, the top 20 individuals in ascending order of the fitness value belong to the top layer TR, the next 30 individuals belong to the middle layer MR, and the remaining 50 individuals belong to the bottom layer BR. Each of these individuals is in a living state. On the other hand, since each breeding area can accommodate 50 individuals respectively, the 30 individuals that are not accommodated in the area of the top layer TR and the 20 individuals that are not accommodated in the area of the middle layer MR are started in a state that is substantially the same as the dead state. It must be noted that, hereinafter, as illustrated in FIG. 3 through FIG. 8, the operation of the pertinent solution search device 100 is performed by repeating the various operations, including the genetic operation, shown in step S7 through step S71 for a prescribed number of times. Thus, a plurality of new target individuals are generated from the plurality of initial target individuals, and again, a plurality of new target individuals are generated from the plurality of target individuals that were generated, and so on.

Here, the CPU 10 samples various types of data for showing transition based on the present program (steps S6 and S7). Specifically, the CPU 10 calculates the average of the score for each layer of TR, MR, and BR, and stores the data (step S6), and then calculates the variance and stores the data (step S7). The data is calculated for verifying (for example, see FIG. 10) the transition of the searching for a solution, and is not used for searching for the solution itself.

Next, the CPU 10 performs the processing for determining whether or not layers need to be exchanged among the layers TR, MR, and BR (step S8 through S10). That is, the CPU 10 determines whether or not to perform the processing using the layer exchange control portion P39. Specifically, first of all, the CPU 10 reads the fitness value (score) average calculation portion P38 of each target individual, and calculates the average value of the score (fitness value) in each layer of TR, MR, and BR, and at the same time, samples the moving average of the average between the generations (step S8). That is, the CPU 10 checks the transition of the average of the score in step S8, and uses it as one of the standards for determining whether or not a radical process (Class Change) involving an exchange of layer must occur. After checking the magnitude of the moving average between generations in step S8, the CPU 10 reads the generations counter E3, and checks whether the current generation count is 60 or above and can be divided out by 60 (step S9). That is, in step S9, from the current generation count and the magnitude of the moving average, the CPU 10 determines whether or not it is timing for a radical process to occur. In step S9, if it is determined that the generation count is 60 or above and can be divided out by 60 (step S9: Yes), the CPU 10 reads the layer exchange control portion P39, and performs the processing for layer exchange (step S10: Layer exchange step). On the other hand, in step S9, if it is determined that the generation count is 60 or above and cannot be divided out by 60 (step S9: No), the CPU 10 moves to the next processing (see FIG. 5) without performing the processing for layer exchange. It must be noted that in step S9, even if the generation count is 60 or above and can be divided out by 60, unless the value of the moving average satisfies a predetermined condition, the CPU 10 may move to the next processing without performing the processing for layer exchange.

In step S9, upon determining that the processing for layer exchange is to be performed, the CPU 10 performs judgment and processing for six types of cases, as the layer exchange step in step S10, as illustrated in FIG. 4. This is because due to the presence of three layers of TR, MR, and BR in the present embodiment, six patterns of vertical relationship among them can be considered. First of all, in the first step of step S10, the CPU 10 determines whether or not the current power relationship is correct. Specifically, the CPU 10 checks whether the score average value of the bottom layer BR is equal to or more than the score average value of the middle layer MR, and also checks whether the score average value of the middle layer MR is equal to or more than the score average value of the top layer TR (step 101*a*). In step 101*a*, if the relationship of magnitude of each score average value is as described above (step 101*a*: Yes), the CPU 10 determines that the power relationship does not change between each layer, and maintains the current relationship between the top and bottom layers (step S102*a*).

Next, upon determining that the relationship shown in step 101*a* is not satisfied (step 101*a*: No), the CPU 10 determines whether another power relationship is established. Specifically, the CPU 10 checks whether the score average value of the middle layer MR is equal to or more than the score average value of the bottom layer BR, and whether the score average value of the bottom layer BR is equal to or more than the score average value of the top layer TR (step 101*b*). In step 101*b*, if the relationship of magnitude of each score average value is as described above (step 101*b*: Yes), the CPU 10 determines that the power relationship between the middle layer MR and the bottom layer BR has reversed, and performs a complete replacement of the individual data in the middle layer MR and the bottom layer BR (step S102*b*).

It must be noted that when the processing of the above step S102*a* is performed, always 'No' is determined in step 101*b*, and therefore, the processing of step S102*b* is not performed.

Next, upon determining that the relationship shown in step 101*b* is not satisfied (step 101*b*: No), the CPU 10 determines whether another power relationship is established. Specifically, the CPU 10 checks whether the score average value of the bottom layer BR is equal to or more than the score average value of the top layer TR, and whether the score average value of the top layer TR is equal to or more than the score average value of the middle layer MR (step 101*c*). In step 101*c*, if the relationship of magnitude of each score average value is as described above (step 101*c*: Yes), the CPU 10 determines that the power relationship between the top layer TR and the middle layer MR has reversed, and performs a complete replacement of the individual data in the top layer TR and the middle layer MR (step S102*c*).

It must be noted that when the processing of the above steps S102*a* and 102*b* is performed, always 'No' is determined in step 101*c*, and therefore, the processing of step S102*c* is not performed.

Next, upon determining that the relationship shown in step 101*c* is not satisfied (step 101*c*: No), the CPU 10 determines whether another power relationship is established. Specifically, the CPU 10 checks whether the score average value of the middle layer MR is equal to or more than the score average value of the top layer TR, and whether the score average value of the top layer TR is equal to or more than the score average value of the bottom layer BR (step 101*d*). In step 101*d*, if the relationship of magnitude of each score average value is as described above (step 101*d*: Yes), the CPU 10 determines that the power relationship among the layers of TR, MR, and BR has reversed so that the layer which was the bottom layer BR has become the highest layer, the layer which was the top layer TR has become the middle layer, and the layer which was the middle layer MR has become the lowest layer, and performs a complete replacement of the individual data in each layer of TR, MR, and BR (step S102*c*). In other words, the individuals of the bottom layer BR are completely replaced with the individuals of the top layer TR such that the individuals which were in the bottom layer BR now belong to the highest layer, the individuals of the top layer TR are completely replaced with the individuals of the middle layer MR such that the individuals which were in the top layer TR now belong to the middle layer, and the individuals of the middle layer MR are completely replaced with the individuals of the bottom layer BR such that the individuals which were in the middle layer MR now belong to the lowest layer.

It must be noted that when the processing of the above steps S102*a* through 102*c* is performed, always 'No' is determined in step 101*d*, and therefore, the processing of step S102*d* is not performed.

Next, upon determining that the relationship shown in step 101*d* is not satisfied (step 101*d*: No), the CPU 10 determines whether another power relationship is established. Specifically, the CPU 10 checks whether the score average value of the top layer TR is equal to or more than the score average value of the bottom layer BR, and whether the score average value of the bottom layer BR is equal to or more than the score average value of the middle layer MR (step 101*e*). In step 101*e*, if the relationship of magnitude of each score average value is as described above (step 101*e*: Yes), the CPU 10 determines that the power relationship of each of the layers TR, MR, and BR has reversed so that the layer which was the bottom layer BR has become the middle layer, the layer which was the middle layer MR has become the highest layer, and the layer which was the top layer TR has become the lowest layer, and performs a complete replacement of the individual data in each layer of TR, MR, and BR (step S102*e*). In other words, the individuals of the bottom layer BR are completely replaced with the individuals of the middle layer MR such that the individuals which were in the bottom layer BR now belong to the middle layer, the individuals of the middle layer MR are completely replaced with the individuals of the top layer TR such that the individuals which were in the middle layer MR now belong to the highest layer, and the individuals of the top layer TR are completely replaced with the individuals of the bottom layer BR such that the individuals which were in the top layer TR now belong to the lowest layer.

It must be noted that when the processing of the above steps S102*a* through 102*d* is performed, always 'No' is determined in step 101*e*, and therefore, the processing of step S102*e* is not performed.

Next, upon determining that the relationship shown in step 101*e* is not satisfied (step 101*e*: No), the CPU 10 determines whether another power relationship is established. Specifically, the CPU 10 checks whether the score average value of the top layer TR is equal to or more than the score average value of the middle layer MR, and also checks whether the score average value of the middle layer MR is equal to or more than the score average value of the bottom layer BR (step 101*f*). In step 101*f*, if the relationship of magnitude of each score average value is as described above (step 101*f*: Yes), the CPU 10 determines that the power relationship between the top layer TR and the bottom layer BR has reversed, and performs a complete replacement of the individual data in the top layer TR and the bottom layer BR (step S102*f*).

It must be noted that when the processing of the above steps S102*a* through 102*e* is performed, always 'No' is determined in step 101*f*, and therefore, the processing of step S102*f* is not performed.

As described above, once all possibilities of reversal of the power relationship are checked, the CPU 10 ends the processing of step S10, and performs the calculation processing of the survival rate of the top layer TR as the next process, as illustrated in FIG. 5 (step S20). It must be noted that the computation result of step S20 is stored in the data region D1 and is used in step S21*cc* (see FIG. 6) described later.

Next, the CPU 10 performs various genetic operations for the bottom layer BR as a genetic operation portion (steps S21*a* through 27*a*: Genetic operation step of bottom layer BR). Specifically, first of all, the CPU 10 determines whether the upper limit of the number of individuals that can survive is reached for each individual belonging to the bottom layer BR (step S21*a*), and if it is determined that the upper limit is reached (step S21*a*: Yes), the CPU 10 reads the thinning-out control portion P31 and performs thinning out in the bottom layer BR until the value reaches below the upper limit (step S22*a*). Thus, for example, a competition for survival is performed based on elitist selection. Specifically, the CPU 10 calculates the score of each individual, and by eliminating, that is, eradicating (killing) the individuals with a bad score (weak individuals) as those that do not satisfy the condition, the number of individuals can be reduced to reach up to the maximum permissible limit of 50 individuals in the bottom layer BR. In other words, only 50 individuals starting from the one with the best score i.e. the smallest score (strong individuals) continue to exist. When the number of individuals is checked or adjusted as described above (step S21*a*: No or step S22*a*), first of all, the CPU 10 determines from among the 50 individuals belonging to the bottom layer BR whether or not one target individual is surviving by checking the life-death information storage region E21 (step S23*a*). As described later, the below operation is performed for all of the 50 individuals belonging to the bottom layer BR. In step S23*a*, if it is determined that the target individual is not surviving, that is, the target individual is in a dead state (step S23*a*: No), the CPU 10 proceeds to the process of crossover using a random number (step S27*a*). On the other hand, in step S23*a*, if it is determined that the target individual is surviving, that is, the target individual is in a living state (step S23*a*: Yes), the CPU 10 further determines whether or not the lifespan of the target individual is less than two times the basic lifespan (five years) by checking the lifespan storage region E24 (step S24*a*), and if it is determined in step S24*a* that the lifespan is less than two times (step S24*a*: Yes), mutation of the gene sequence of the target individual occurs. That is, the gene sequence of the individual is rearranged with a fixed probability (step S25*a*). It must be noted that, in step S24*a*, if it is determined that the lifespan of the target individual is two times or more of the basic lifespan (step S24*a*: No), mutation does not occur in order to maintain the gene sequence of an individual with a long life having a relatively good fitness value, and the CPU 10 proceeds to the next processing. After passing through steps S24*a* and S25*a*, the CPU 10 functions as an information writing portion and writes the various types of information about the target individual having new genetic information in each region E21 and E22, for example, of the individual data storage region E2, which is the information storage portion, and at the same time (information writing step), reads the fitness value calculation portion P2, calculates the fitness value, that is, the score, and writes the obtained value in the fitness value information storage region E23 of the individual data storage region E2 (step S26*a*: Fitness value calculation step). In addition, the CPU 10 performs crossover using a random number (step S27*a*).

In this case, the crossover in step S27*a* is performed by appropriately rearranging the gene sequences of two individuals. Specifically speaking, first of all, as illustrated in FIG. 9A and FIG. 9B, the individuals to be crossed over are a first individual IN1 and a second individual IN2, and in addition, the sequence elements of the gene sequence of the first individual IN1 are GN1' through GNx', and the sequence elements of the gene sequence of the second individual IN2 are GN1" through GNx". Here, in a first method of the crossover of the first individual IN1 and the second individual IN2, it is considered that a random number is used and the sequence element up to which interception is performed is determined, and the sequence elements of each individual are rearranged. For example, as illustrated in the figure, when a random number is used and it is determined that sequence elements up to the third element are separated and rearranged, a new individual IN3 having the sequence elements GN1' through GN3' and GN4" through GNx" as illustrated in FIG. 9C is generated by the crossover, or conversely from the individual IN3, a new individual IN4 having the sequence elements GN1" through GN3" and GN4' through GNx' as illustrated in FIG. 9D is generated. In case of the crossover with the first method described above, the new individuals IN3 and IN4 inherit the information of both the first individual IN1 and the second individual IN2 to some extent, and therefore, this method of crossover can be said to retain the genetic characteristics relatively strongly.

Furthermore, as illustrated in FIG. 9E, a second method that is different from the above-described first method can be used to generate a new individual IN5 by determining one-by-one which sequence element to select, based on the random number, from each of the corresponding gene sequences of the first individual IN1 and the second individual IN2, for example. That is, first of all, the random number is used to select any one sequence element from the sequence element GN1', which is the first sequence element of the first individual IN1 and the sequence element GN1", which is the first sequence element of the second individual IN2, and the selected sequence element is the first sequence element of the new individual IN5. Thereafter, the second sequence element onwards is also determined in the same way and the gene sequence of the new individual is set. In the case of crossover according to the second method, contrary to the crossover according to the above-described first method, although the new individual IN5 has close to an almost random gene sequence, the new individual is not necessarily completely unaffected by the first and the second individuals IN1 and IN2, and inherits the information in an indirect and potential manner.

Furthermore, the above-described first method and second method can also be combined together. For example, a method in which the above-described first method and the second method are combined together in a 1:1 ratio can be used for crossover in step S27*a*. Thus, the diversity of a species is secured by being able to generate a new individual in which genetic characteristics are retained to a large extent as well as a new individual that does not retain such genetic characteristics to a large extent.

Coming back to FIG. 5, after step S27*a*, the CPU 10 checks the optimal fitness value, which is the smallest fitness value of the bottom layer BR (step S28*a*). That is, the CPU 10 compares the fitness value of one target individual that has passed through the above steps S23*a* through S27*a*, and the fitness value of an individual having the genetic information that is stored in the optimal fitness value storage region E2*x*, and sets the smaller value as the new smallest fitness value. Here, in addition to the information about the existing individuals, the optimal fitness value storage region E2$x$ stores information about the individual having the smallest fitness value from among the individuals existing in each layer of TR, MR, and BR until then. That is, the optimal fitness value storage region E2$x$ contains information that acts as a candidate solution to the problem of TSP, etc., which is the final objective. Therefore, if the target individual has an fitness value that is equal to or lower than the fitness values stored until then in the optimal fitness value storage region E2$x$, the CPU 10 determines the target individual as a new candidate pertinent solution and writes the genetic information of the target individual in the optimal fitness value storage region E2$x$. If the fitness value of the target individual is larger than the smallest fitness value until then, the CPU 10 performs the processing of retaining the genetic information of the individual that was stored until then. Thus, the CPU 10 can always record the genetic information of the individual having the smallest fitness value from among the individuals of successive generations existing in the bottom layer BR, in the optimal fitness value storage region E2$x$ (successive-generation fitness value recording step).

Next, the CPU 10 functions as a genetic operation portion and performs various genetic operations for the middle layer MR (steps S21$b$ through 27$b$: Genetic operation step of middle layer MR). Specifically, first of all, the CPU 10 determines for each individual belonging to the middle layer MR whether the upper limit of the number of individuals that can survive is reached (step S21$b$), and if it is determined that the upper limit is reached (step S21$b$: Yes), the CPU 10 reads the predation activity control portion P34 and performs the predation operation (step S22$b$: Predation step). That is, a change in the living state and death as a result of the action of eating and being eaten is seen in the individuals of the middle layer MR and the bottom layer BR, which is a point specific to CDS. Specifically, based on a random number, an individual belonging to the middle layer MR and an individual belonging to the bottom layer BR are selected, the scores of both the individuals are read and compared, and if the score of the individual of the middle layer MR is equal to or lower than the score of the individual of the bottom layer BR, the individual of the bottom layer BR that is preyed upon moves to a dead state as a result of the success in predation, and if the score of the individual of the middle layer MR is more than the score of the individual of the bottom layer BR, the individual of the middle layer MR moves to a dead state as a result of failure in predation. Thus, the number of individuals in the middle layer MR is adjusted. As a result of the change in the living state and death seen in the predation step, the CPU 10 rewrites the information stored in the life-death information storage region E21.

When the number of individuals is checked or adjusted (step S21$b$: No or step S22$b$), then same as in the case of the bottom layer BR (see steps S23$a$ through 28$a$), the determination of survival of one target individual belonging to the middle layer BR (step S23$b$), the determination of the lifespan (step S24$b$), the mutation process (step S25$b$), the fitness value (score) calculation (step S26$b$) process, and the crossover process (step S27$b$) are performed, and finally, the CPU 10 checks the optimal fitness value of the middle layer MR (step S28$b$). When the genetic information changes as a result of the above operation, the data in the individual data storage region E2 is appropriately rewritten accordingly. Furthermore, the specific process of crossover of step S27$b$ can be performed in the same way as the above-described step S27$a$.

Next, the CPU 10 functions as a genetic operation portion and performs various genetic operations for the top layer TR (steps S21$c$ through 27$c$: Genetic operation step of top layer TR). Specifically, first of all, the CPU 10 determines for each individual belonging to the top layer TR whether the upper limit of the number of individuals that can survive is reached (step S21$c$), and if it is determined that the upper limit is reached (step S21$c$: Yes), the CPU 10 further reads the calculation result obtained in step S20 and checks whether the survival rate of the individuals belonging to the top layer TR has reached the upper limit (step S21$cc$). In step S21$cc$, if it is determined that the upper limit is reached, the CPU 10 performs thinning out in the top layer TR until the survival rate becomes lower than the upper limit (step S22$c$). Specifically, for example, thinning out is performed based on elitist selection same as in the case of step S22$a$. Once the survival rate of the individual is below the upper limit (step S21$cc$: No or step S22$c$), the predation operation is performed (step S22$cc$). That is, a change in the living state and death as a result of the action of eating and being eaten is seen in the individuals of the top layer TR and the middle layer MR. Specifically, based on a random number, an individual belonging to the top layer TR and an individual belonging to the middle layer MR are selected, the scores of both the individuals are read and compared, and if the score of the individual of the top layer TR is equal to or higher than the score of the individual of the middle layer MR, the individual of the middle layer MR that is preyed upon moves to a dead state as a result of the success in predation, and if the score of the individual of the top layer TR is less than the score of the individual of the middle layer MR, the individual of the top layer TR moves to a dead state as a result of failure in predation. Thus, the number of individuals in the top layer TR is adjusted. As an example, the upper limit of the survival rate of individuals is set to 50 individuals.

When the number of individuals in the top layer TR is checked or adjusted (step S21$c$: No or step S22$cc$), then same as in the case of the bottom layer BR (see steps S23$a$ through 28$a$), the determination of survival of one target individual belonging to the top layer TR (step S23$c$), the determination of the lifespan (step S24$c$), the mutation process (step S25$c$), the fitness value (score) calculation (step S26$c$) process, and the crossover process (step S27$c$) are performed, and finally, the CPU 10 checks the optimal fitness value of the top layer TR (step S28$c$). Furthermore, the specific process of crossover of step S27$c$ can be performed in the same way as the above-described step S27$a$.

The CPU 10 performs the above checking process for each individual belonging to each layer of TR, MB, and BR. That is, the CPU 10 checks whether the number of the above-mentioned checking processes for each individual has reached the maximum number of individuals that can be bred, that is, the number has reached 50 times, which is set as the number of individuals of each breeding area (step S40), and repeats the processes in the above step S21$a$ through step S28$c$ until it is determined that the maximum number of individuals are reached.

In step S40, if it is determined that the maximum number of individuals is reached (step S40: Yes), the CPU 10 reads the lifespan control portion P36, and one-by-one reduces the lifespan of all individuals of the top layer TR, the middle layer MR, and the bottom layer BR (steps S50 through S52). That is, along with rewriting the information stored in the lifespan storage region E24, if the lifespan of any individual is over and the dead state is reached, the CPU 10 rewrites the living state and death in the life-death information storage region E21.

Next, with regard to the middle layer MR and the bottom layer BR constituting the prey side in the predation step, in order to read the extinction avoiding control portion P35 and determine whether or not to perform the processing for causing a phenomenon equivalent to biological explosion, the CPU 10 checks the life-death information storage region E21, and counts the number of surviving individuals in each of the middle layer MR and the bottom layer BR (step S60, S61).

As a result of step S60, the CPU 10 determines whether or not the number of surviving individuals in the middle layer MR has reduced below the survivable limit, which is a prescribed number with respect to the maximum number of 50 (step S62*a*). The survivable limit is half the total number of individuals in each layer. In step S62*a*, if it is determined that the number of surviving individuals is not below the survivable limit (step S62*a*: No), the CPU 10 determines that there is no need to cause a phenomenon equivalent to biological explosion, and moves to the processing for the number of individuals in the bottom layer BR. On the other hand, in step S62*a*, if it is determined that the number of surviving individuals is below the survivable limit (step S62*a*: Yes), the CPU 10 reads the extinction avoiding control portion P35, and performs the processing to tremendously increase the number of individuals in the middle layer MR (extinction avoiding step). First of all, the CPU 10 determines whether one target individual belonging to the middle layer MR is dead or not (step S63*a*). If it is determined that the target individual is in a dead state, that is, the target individual is not surviving (step S63*a*: Yes), the CPU 10 generates one individual having a new gene sequence using a random number (step S64*a*) and replaces it to the dead individual. That is, in addition to the information about the gene sequence of the new generated individual, the CPU 10, for example, calculates the score of the generated individual (step S65*a*), writes the information obtained in the fitness value information storage region E23, for example, of the individual data storage region E2, and checks whether the operation of step S63*a* through step S65*a* has reached a prescribed 50 times, which is set as the number of individuals of the breeding area (step S66*a*). That is, the CPU 10 determines whether survival of all individuals belonging to the middle layer MR has been checked. On the other hand, in step S62*a*, if it is determined that the target individual is not dead, that is, the target individual is surviving, the CPU 10 does not generate a new individual as described above, and performs the operation of step S66*a*. That is, the viable number that is necessary for avoiding extinction is set as 50, which is the maximum number of surviving individuals, and by performing the above operation up to 50 times, a phenomenon equivalent to biological explosion is performed.

In step S66*a*, once the survival of all individuals belonging to the middle layer MR has been checked (step S66*a*: Yes), the process of increasing the number of individuals in the middle layer MR ends, and the same process is performed for the individuals belonging to the bottom layer BR (steps S62*b* through 66*b*). That is, the CPU determines whether or not the number of surviving individuals in the bottom layer BR has reduced below a prescribed survivable limit (step S62*b*), checks the living state and dead state of the target individual (step S63*b*), and if dead, generates one individual having a new gene sequence by using a random number (step S64*b*), and collects the data of the individual and then, replaces it to the dead individual (step S65*b*). In addition, the CPU 10 checks whether the above process has been performed a prescribed number of times (step S66*b*).

Next, the CPU 10 performs the process of updating the generation (step S70). That is, the CPU 10 reads the generation update portion P37, adds up the value of the generations counter E3 by one, and performs the process for updating the generation of the entire system constructed in the present embodiment by one. It must be noted that as a result of the process in steps S50 through S52, along with an update of the generation in step S70, the lifespan of each individual is reduced one by one. In other words, with each passing year, each one of all individuals becomes older. Next, the CPU 10 reads the generations counter E3, and determines whether or not the generation update count has reached the upper limit (step S71). If the update count has not reached the upper limit (step S70: No), the CPU 10 functions as a reprocessing portion, and repeats the processes from step S6 (see FIG. 3) through step S70 (reprocessing step). If the update count has reached the upper limit (step S70: Yes), the CPU 10 reads the optimal fitness value of each of the top layer TR, the middle layer MR, and the bottom layer BR from the optimal fitness value storage region E2*x*, which is the candidate solution storage portion, and outputs each value (step S80 through step S82). Each value output in step S80 through step S82 is an element of the candidate solution of the target problem. From the optimal fitness values, the CPU 10 outputs a single value or multiple values as the pertinent solution, which is a candidate solution to the searched problem (step S83: Candidate solution extraction step).

Furthermore, in the above case, in steps S28*a*, S28*b*, and S28*c*, not only the fitness values of the existing individuals, but the genetic information of the individual having the smallest value from among the fitness values of the individuals existing in each layer of TR, MR, and BR of successive generations is stored in the optimal fitness value storage region E2*x*. Therefore, even though the diversity of the existing individuals is maintained, it becomes possible to search for a candidate solution, to a problem, with the highest adaptability (fitness value) within the search conducted until then (successive-generation fitness value recording step).

Figure 10:
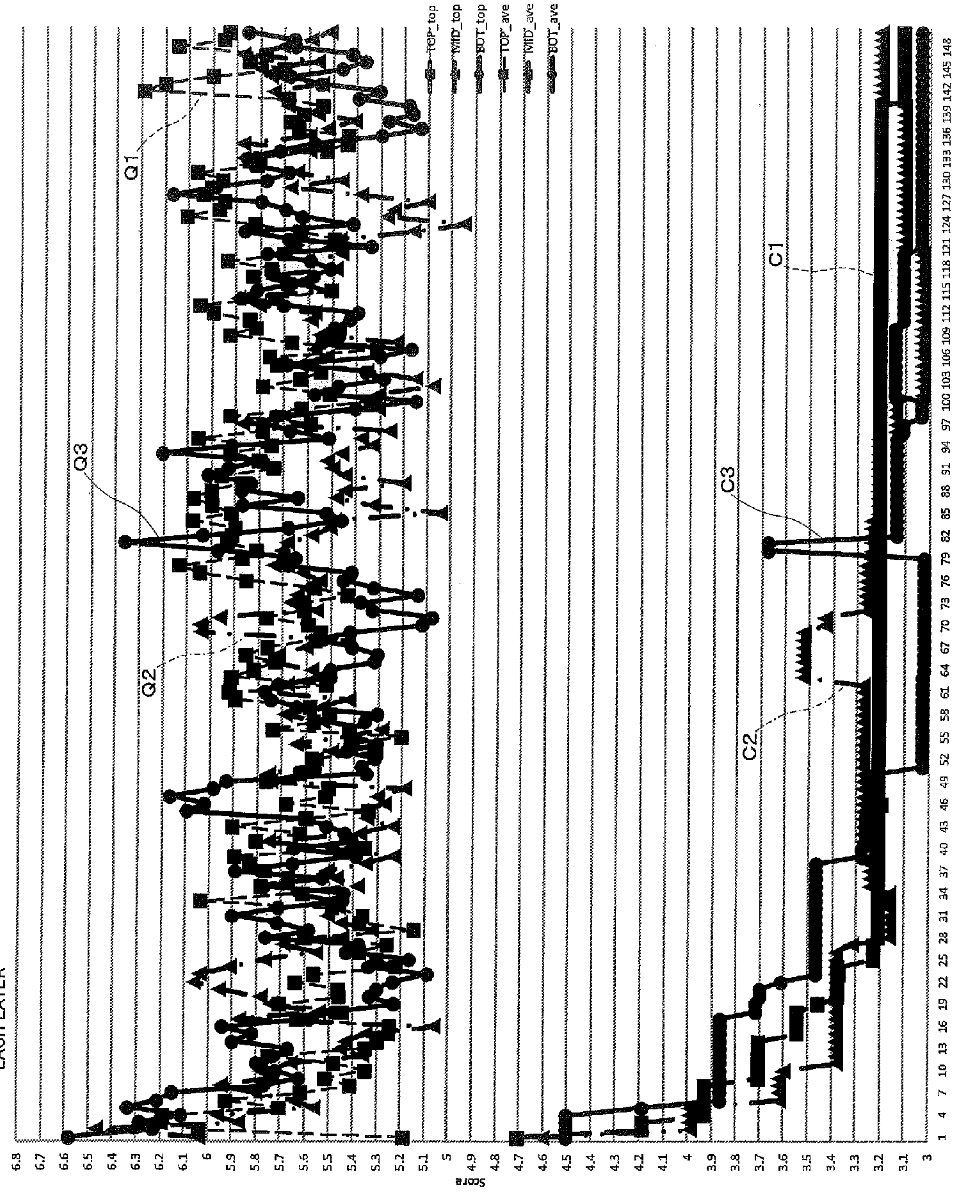
FIG. 10 is a graph illustrating the result of an example using the search method of a pertinent solution according to an embodiment.

FIG. 10 is a graph of an example illustrating a pertinent solution obtained from a search performed by using the pertinent solution search device 100 having a program such as that described above. The horizontal axis shows the update count, that is, the number of generations, and the vertical axis shows the value of the score, for example. As already described above, in the present embodiment, among multiple individuals, the individual having the smallest score has the best fitness value. Furthermore, in the graph illustrated in FIG. 10, the data obtained in steps S6 and S7, for example, can be output and displayed by the display device 12.

In FIG. 10, broken lines C1, C2, and C3 respectively show the transition of the smallest fitness value (score) in each generation of the top layer TR, the middle layer MR, and the bottom layer BR. In such a case, the broken line C3 for the bottom layer BR shows the best fitness value of "3.019338" in successive generations at the generations 64 through 79. That is, in such a case, in the generations 64 through 79, the gene sequence of an individual belonging to the bottom layer BR and having the smallest fitness value is output as the pertinent solution, which is a candidate solution to the set problem. Furthermore, from the transition of the broken lines C1, C2, and C3, it is understood that the relationship between the high and low values of the optimum score in each layer is replaced appropriately, and the diversity of the individual is maintained.

Furthermore, in FIG. 10, the broken lines Q1, Q2, and Q3 respectively show the transition of the average value of the score in each layer of TR, MR, and BR. From the transition of the broken lines Q1, Q2, and Q3, it is understood that the average value of the score is not a constant value, and is maintained in an appropriately distributed state. This also indicates that the diversity of the individuals is maintained.

Figure 11A:
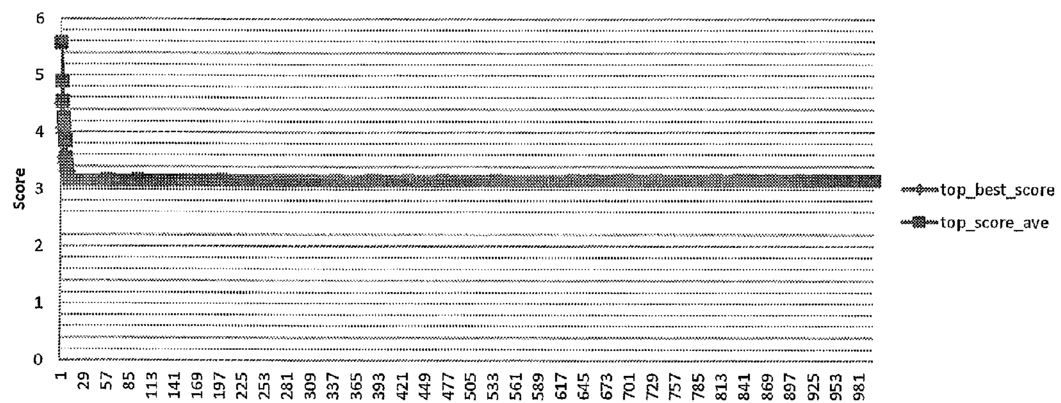
FIG. 11A and FIG. 11B are graphs illustrating the result of an example of a comparative example.
Figure 11B:
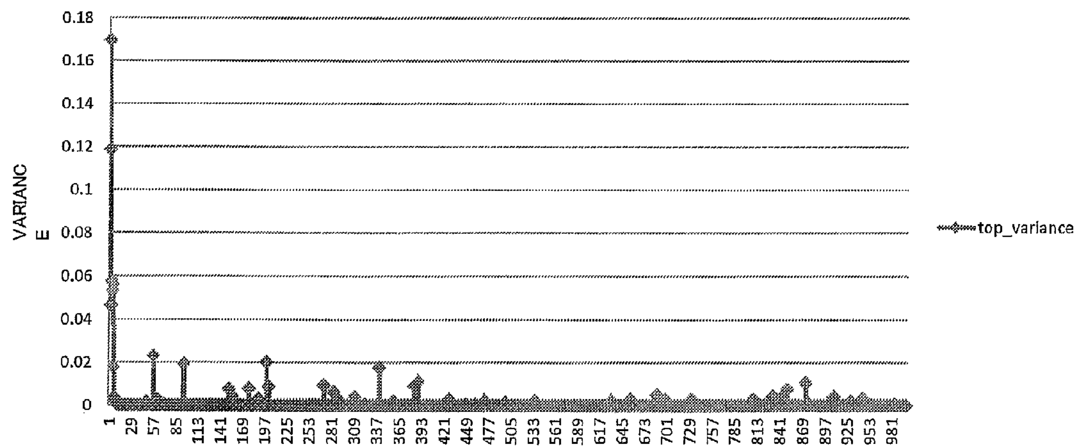

FIG. 11A and FIG. 11B are diagrams that are shown as comparative examples, and are the result of searching for a solution to the same problem as in FIG. 10 by general GA. FIG. 11A shows the average value of the score and the smallest fitness value, and FIG. 11B shows the variance of the smallest fitness value. In the comparative examples, the fluctuation in the broken line for the best smallest fitness value and the average thereof, or the broken line for the variance immediately becomes less, thus indicating an almost same value, and a rapid loss of diversity.

As described above, in the present embodiment, the information about the living state and the dead state is included as one of the genetic information items regarding a plurality of individuals. That is, the information is stored in the lifespan storage region E24 of the individual data storage region E2. Thus, even if an individual has a relatively good fitness value (adaptability), or an fitness value (adaptability) that is not good, each individual is finally culled out (selected) by meeting death, and therefore, for example, the creation of an oligopoly situation by individuals having an fitness value that is relatively good but not to the extent of a pertinent solution is not seen, and the issue of being led to a local minimum while searching for a pertinent solution, which is a candidate solution to a set problem is avoided.

Second Embodiment

Hereinafter, a search method of a pertinent solution according to a second embodiment will be described. The present embodiment is a modification of the search method of a pertinent solution according to the first embodiment, and the parts and items that are not particularly described are the same as the first embodiment.

Figure 12:
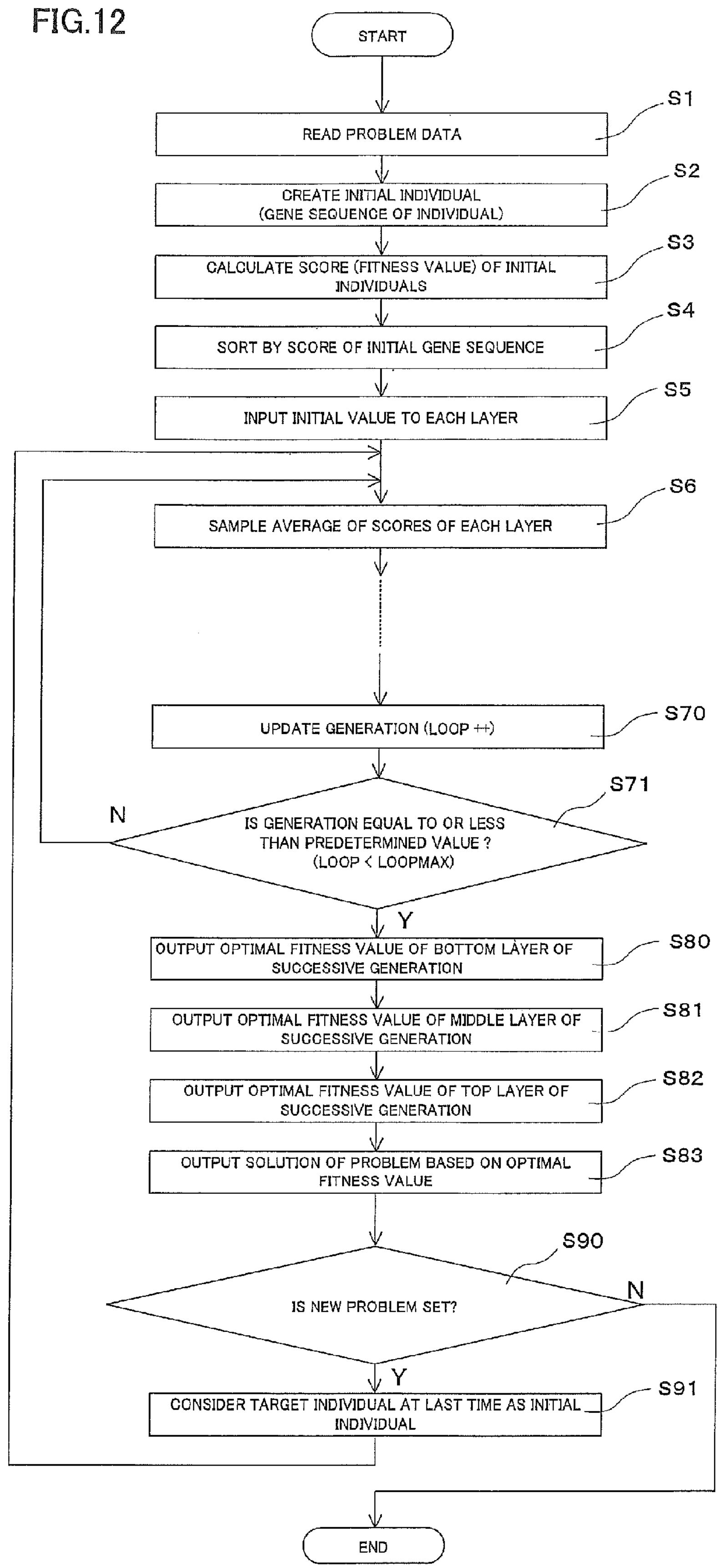
FIG. 12 is a flowchart that conceptually explains a search method of a pertinent solution according to a second embodiment.

FIG. 12 is a flowchart that conceptually explains the search method of a pertinent solution according to the present embodiment. The pertinent solution search device for executing the operation is the same as the pertinent solution search device 100 shown in FIG. 1A, and therefore, the illustrations and explanation are omitted.

The present embodiment is a modification of the first embodiment, and is an example of the case of handling problems that time series change, such as those where after searching for a solution to a problem, for example, each parameter, for example, for setting a new problem is modified and the solution to the new problem is searched. Specifically, the processing from the processing of reading the problem data, which is the initial processing of the first problem (step S1) up to the process of output of the candidate solution to the problem, which is the last process (step S83), is performed in the same way as the first embodiment. Thus, the candidate pertinent solution of the problem set initially is output. Next, the CPU 10 (see FIG. 1A) determines whether or not a new problem that is different from the initially set problem has been set (step S90: New search setting step). That is, the CPU 10 checks whether the problem data such as each parameter for setting a new problem has been input via the input device 11 by an operator. If it is determined that the settings for a new problem are not made (step S90: No), the CPU 10 determines that all problems to be searched are complete, and ends the process. On the other hand, if it is determined that the settings for a new problem are made (step S90: Yes), the CPU 10 performs processing for handling the information about each individual belonging to each layer at the time of execution of step S83 as the information about the initial individuals (step S91). That is, the processing of step S90 and step S91 corresponds to the processing of step S1 through step S5, and thus, by handling each individual at the time of execution of step S83 as the target individual for which genetic operation is to be performed, the pertinent solution to a new problem can be searched without again making initial settings for the individuals. For example, in TSP (Traveling Salesman Problem), when the arrangement of cities is different and the relationship of the distance between cities at the time of traveling is different in the initial (the first) problem and the next (second) problem, then after searching for the candidate solution to the first problem, if only the method of calculating the distance between cities, that is, the method of calculating the fitness value in the second problem is reset in step S90 and step S91, the individual information of the first problem can be applied as is without having to reset an individual, and approach the second problem quickly.

As described above, in the present embodiment, by further including a new search setting step of setting a new problem after determining the candidate solution to a problem, as well as using the multiple target individuals at the time of determining the candidate previous solution as the multiple initial individuals generated in the initial individual generating step, in situations where the characteristics of a problem time series change, such as when the solution to a new problem is to be searched after searching for the candidate solution to one problem, the new problem can be handled without making the initial settings for multiple individuals, again.

The present invention is not limited to the above embodiments, and various other changes may be applied to other configurations without departing from the content and scope of the present invention.

First of all, in the above embodiments, all specified numeric values are examples, for example, a system having multiple layers was described as a three-hierarchy configuration having a top layer TR, a middle layer MR, and a bottom layer BR, however, the system is not limited to three layers, and may have a structure comprising five or above layers, for example. On the contrary, the system need not necessarily have multiple layers, that is, the system may have one, that is, a single layer. Furthermore, among the top layer TR, the middle layer MR, and the bottom layer BR, the relationship of a predator and a prey was explained only between the top layer TR and the middle layer MR, and between the middle layer MR and the bottom layer BR, however, an aspect in which the relationship of a predator and a prey exists even between the top layer TR and the bottom layer BR is also possible. Furthermore, the number of individuals belonging to each breeding area was set as 50, however, this number also can be changed appropriately, for example, the number of individuals may be more than 50. Furthermore, the lifespan of individuals was also specified to be of three types, namely a normal lifespan (five years), a long lifespan (15 years), and a short lifespan (two years), however, various patterns with a different number of types and differences in lifespan may be considered.

Furthermore, as described above, each of multiple individuals has a female gender or a male gender, and male selection may be included in the genetic operation step. In such a case, for example, a battle for survival is initiated by comparing the fitness values between male individuals from among the target individuals such that male selection seen in nature can be mimicked. In such a case, the information about female and male individuals is also stored in the individual data storage region E2.

Furthermore, among the descriptions provided above, the description about crossover in step S27*a*, etc. is not limited to the above first method and second method. For example, according to the first method, a separation is provided at one location with respect to the sequence elements such as GN1' that are arranged as a gene sequence and the gene sequence is rearranged, however, a method in which a separation is provided at multiple locations and the gene sequence is rearranged may be adopted, and such a method may be combined with other methods as well. Furthermore, the proportion in the case of combination of multiple methods can also be determined appropriately.

Furthermore, in the above description, for example, after performing the processing up to counting of the number of surviving individuals in the bottom layer BR in step S61, if the number is determined to be constant, then a step of forcibly thinning out a certain proportion of individuals having information that is close to best from among individuals surviving in the top layer TR may be further added. Specifically, for example, after repeating the processing of step S61, at every 10th time, the information of an individual having the best fitness value (score) from among the individuals belonging to the top layer TR is compared with the information of other individuals at that time, and individuals for which more than 70% of the content of the genetic information is same as the individuals having the best fitness value (score) are eradicated (killed) unconditionally. By adding such a thinning out process, the possibility of being led to a local minimum can be reduced.

Furthermore, in the above descriptions, the individuals in the top layer TR constituting the highest layer are not eaten and the individuals in the bottom layer BR constituting the lowest layer do not eat. When a radical process (Class Change) involving an exchange of layer occurs, layers are replaced, and therefore, after the exchange of layers, the individuals in the top layer TR constitute the eating side and the individuals in the bottom layer BR constitute the side that is eaten. However, in addition to above, a concept in which the individuals in the lowest layer eat the individuals in the highest layer may also be incorporated. In other words, in the above descriptions, the relationship between eating and being eaten was performed in a hierarchical order from the highest position to the lowest position, however, a loop-like structure may also be formed by adding an element whereby the individuals at the lowest position eat the individuals at the highest position.

Furthermore, as already described, not only TSP (Traveling Salesman Problem), but various types of problems can be handled in the same way as a general GA by using the pertinent solution search device 100 of the present embodiment. In addition, due to the fact that by using the pertinent solution search device 100, the solution to problems that time series change can be searched without resetting the initial settings again, search can be performed faster than in the case of the general GA.

Furthermore, depending on the purpose of use, a system can be constructed through partial adoption of the means included in the pertinent solution search device 100.

Examples of application of the pertinent solution search device 100 of the present embodiment include the search for a pertinent solution to a problem of finding a processing pattern for the shortest wiring length when multiple terminals are to be wired in a specified combination in wirings such as IC chips, for example. Furthermore, for example, when performing the business of door-to-door delivery, the selection of a more preferable sequence pattern from among the sequence patterns of traveling to the delivery destinations, and the selection of a more efficient way of division of labor when performing division of labor in a certain task can be executed quickly by using the pertinent solution search device 100.

The invention claimed is:

1. A search method of a pertinent solution using a genetic algorithm that performs genetic operation including selection, mutation, and crossover of a plurality of individuals each having an element of a candidate solution to a problem in the form of a gene sequence, the method comprising:

initial creating a plurality of initial individuals and using the plurality of initial individuals as a plurality of target individuals that are a target of processing;

storing, in an information storage portion, genetic information about the plurality of target individuals as a plurality of existing target individuals;

generating a plurality of new target individuals from the plurality of existing target individuals by performing at least one genetic operation among selection, mutation, and crossover for at least one of the plurality of existing target individuals;

writing, to the information storage portion, the genetic information about the plurality of new target individuals generated in the at least one genetic operation;

calculating a fitness value corresponding to the candidate solution to the problem on the basis of the gene sequence of each of the plurality of initial individuals and the plurality of new target individuals;

a reprocessing step of repeating the generating and the calculating for the plurality of new target individuals; and setting at least one value with a highest adaptability among plural fitness values obtained in the calculating that is repeated plural times, as one of the candidate solutions to the problem, wherein the information storage portion includes, as one of the items of the genetic information about the plurality of target individuals, information about whether all individuals are in which state among a state that is a target of genetic operation in the generating and a target of the calculation of the fitness value in the calculating, and a dead state that is not the target of genetic operation nor the target of the calculation of the fitness value, wherein in the initial creating and the generating, a plurality of layers, where the plurality of target individuals can be retained up to a predetermined number, are provided, wherein a breeding area is composed of the plurality of layers, and at least one of the plurality of layers has a relatively high ranking and at least another one of the plurality of layers has a relatively low ranking, and a predation of leading an individual belonging to a lower layer to a dead state due to predation by an individual belonging to a higher layer in the breeding area constitutes an aspect of the generating, wherein in the calculating, a check of an optimal fitness value is performed for all of the plurality of layers constituting the breeding area respectively, and further comprising:

completely replacing the individuals belonging to one layer with individuals belonging to another layer under predetermined conditions.

2. The search method of a pertinent solution according to claim 1, wherein each of the plurality of target individuals has a predetermined value of a lifespan, and additionally comprising updating a generation of the plurality of target individuals in correspondence to the generating and reducing the lifespan.

3. The search method of a pertinent solution according to claim 2, wherein the lifespan of the plurality of target individuals differs among individuals depending on the fitness value of each individual.

4. The search method of a pertinent solution according to claim 1, wherein individuals belonging to different layers in the breeding area do not cross over, and crossover occurs only between individuals belonging to a same layer.

5. The search method of a pertinent solution according to claim 1, wherein in the predation, when one individual of the higher layer is successful in predation of one individual of the lower layer, the individual of the lower layer that is preyed upon reaches the dead state, and in the case of failure in predation, the individual of the higher layer that has failed in predation reaches the dead state.

6. The search method of a pertinent solution according to claim 5, wherein in the predation, the success or failure in predation is determined, by the adaptability of the fitness value of each individual.

7. The search method of a pertinent solution according to claim 1, further comprising:

increasing a number of individuals belonging to a layer up to a predetermined viable number, when the number of individuals belonging to the layer has reduced below a predetermined survivable limit, in the breeding area.

8. The search method of a pertinent solution according to claim 1, further comprising:

recording, in the information storage portion, all fitness values obtained by repeating the calculating, wherein among all the fitness values recorded in the recording, a value with the highest adaptability is set as a candidate solution to the problem.

9. The search method of a pertinent solution according to claim 1, wherein, the predetermined conditions of the completely replacing the individuals is with reference to an average value of the fitness values of individuals belonging to the plurality of layers constituting the breeding area.

10. The search method of a pertinent solution according to claim 1, further comprising:

setting a new problem after determining the candidate solution to the problem, as well as using the plurality of target individuals at the time of determining the previous candidate solution as the plurality of initial individuals created in the initial creating.

11. The search method of a pertinent solution according to claim 1, wherein each of the plurality of target individuals has a female or a male gender, and the generating includes male selection.

12. A pertinent solution search device using a genetic algorithm that performs genetic operation including selection, mutation, and crossover of a plurality of individuals each representing an element of a candidate solution to a problem in the form of a gene sequence, the pertinent solution search device comprising:

a central processing unit;

an initial individual generating portion, operating with the central processing unit, that generates a plurality of initial individuals and uses the plurality of initial individuals as a plurality of target individuals that are a target of processing;

an information storage portion connected with the central processing unit and that stores genetic information about the plurality of target individuals as a plurality of existing target individuals;

a genetic operation portion, operating with the central processing unit, that generates a plurality of new target individuals from the plurality of existing target individuals by performing at least one genetic operation among selection, mutation, and crossover for at least one of the plurality of existing target individuals;

an information writing portion, operating with the central processing unit, that writes, to the information storage portion, the genetic information about the plurality of new target individuals generated by the genetic operation portion;

a fitness value calculation portion, operating with the central processing unit, that calculates a fitness value corresponding to the candidate solution to the problem on the basis of the gene sequence of each of the plurality of initial individuals and the plurality of new target individuals;

a reprocessing portion, operating with the central processing unit, that repeats the processing performed by the genetic operation portion and the fitness value calculation portion for the plurality of new target individuals; and a candidate solution storage portion, operating with the central processing unit, that stores at least one value with the a highest adaptability among the multiple fitness values obtained in the fitness value calculation portion by repeating the processing multiple times, as one of the candidate solutions to the problem, wherein the information storage portion includes, as one of the items of the genetic information about the plurality of individuals, information about whether all individuals are in which state among a living state that is a target of genetic operation in the genetic operation portion and a target of the calculation of the fitness value in the fitness value calculation portion, and a dead state that is not the target of genetic operation nor the target of the calculation of the fitness value, wherein in the initial individual generating portion and the genetic operation portion, a plurality of layers, where the plurality of target individuals can be retained up to a predetermined number, are provided, wherein a breeding area is composed of the plurality of layers, and at least one of the plurality of layers has a relatively high ranking and at least another one of the plurality of layers has a relatively low ranking, and a predation of leading an individual belonging to a lower layer to a dead state due to predation by an individual belonging to a higher layer in the breeding area constitutes an aspect of the generating, wherein in the fitness value calculation portion, a check of an optimal fitness value is performed for all of the plurality of layers constituting the breeding area respectively, and further comprising:

a replacing portion, completely replacing the individuals belonging to one layer with individuals belonging to another layer under predetermined conditions.

13. The search method of a pertinent solution according to claim 1, wherein the breeding area is composed of a three layers.

14. The search method of a pertinent solution according to claim 13, wherein each of the plurality of target individuals has a predetermined value of a lifespan, and additionally comprising updating a generation of the plurality of target individuals in correspondence to the generating and reducing the lifespan.

15. The search method of a pertinent solution according to claim 14, wherein the predetermined conditions of the completely replacing the individuals is with reference to an average value of the fitness values of individuals belonging to the plurality of layers constituting the breeding area.

16. The search method of a pertinent solution according to claim 1, wherein all individuals are in one of states among the living state or the dead state, regardless of their fitness values.

17. The pertinent solution search device according to claim 12, wherein the breeding area is composed of a three layers, wherein each of the plurality of target individuals has a predetermined value of a lifespan, and additionally comprising an updating portion, updating a generation of the plurality of target individuals in correspondence to the generating and reducing the lifespan.

* * * * *